(12) United States Patent
Meyer et al.

(10) Patent No.: US 10,898,142 B2
(45) Date of Patent: *Jan. 26, 2021

(54) CARDIAC RESPONSE CLASSIFICATION USING RETRIGGERABLE CLASSIFICATION WINDOWS

(71) Applicant: Cardiac Pacemakers, Inc., St. Paul, MN (US)

(72) Inventors: Scott A. Meyer, Lakeville, MN (US); Yanting Dong, Lexington, KY (US); Jeremy J. Maniak, Columbia Heights, MN (US); Doug Birholz, Shoreview, MN (US); John M. Voegele, East Bethel, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 355 days.

This patent is subject to a terminal disclaimer.

(21) Appl. No.: 15/970,573

(22) Filed: May 3, 2018

(65) Prior Publication Data

US 2018/0249963 A1 Sep. 6, 2018

Related U.S. Application Data

(63) Continuation of application No. 12/818,066, filed on Jun. 17, 2010, now Pat. No. 9,993,205, which is a
(Continued)

(51) Int. Cl.
*A61B 5/00* (2006.01)
*A61N 1/37* (2006.01)
*A61B 5/0452* (2006.01)

(52) U.S. Cl.
CPC ............ *A61B 5/7264* (2013.01); *A61N 1/371* (2013.01); *A61B 5/04525* (2013.01); *A61B 5/7217* (2013.01)

(58) Field of Classification Search
CPC ......... A61B 5/7264; A61N 1/371; A61N 1/08
See application file for complete search history.

(56) References Cited

U.S. PATENT DOCUMENTS

| 3,782,367 | A | 1/1974 | Hochberg et al. |
| 3,920,005 | A | 11/1975 | Gombrich et al. |
(Continued)

FOREIGN PATENT DOCUMENTS

| EP | 0468720 | A2 | 1/1992 |
| EP | 0560569 | A2 | 9/1993 |
(Continued)

OTHER PUBLICATIONS

"U.S. Appl. No. 10/734,599, 312 Amendment filed Jun. 9, 2010", 4 pgs.
(Continued)

*Primary Examiner* — Alyssa M Alter
(74) *Attorney, Agent, or Firm* — Schwegman Lundberg & Woessner, P.A.

(57) ABSTRACT

Methods and devices for classifying a cardiac response to pacing involve establishing a retriggerable cardiac response classification window. A first cardiac response classification window is established subsequent to delivery of a pacing pulse. A cardiac signal following the pacing stimulation is sensed in the first classification window. A second cardiac response classification may be triggered if a trigger characteristic is detected in the first classification window. The cardiac signal is sensed in the second classification window if the second classification window is established. The cardiac response to the pacing stimulation is determined based on characteristics of the cardiac signal. The cardiac response may be determined to be one of a captured
(Continued)

response, a non-captured response, a non-captured response added to an intrinsic beat, and a fusion/pseudofusion beat, for example.

20 Claims, 23 Drawing Sheets

Related U.S. Application Data continuation of application No. 10/734,599, filed on Dec. 12, 2003, now Pat. No. 7,774,064.

(56) References Cited

U.S. PATENT DOCUMENTS

| | | | |
|---|---|---|---|
| 4,023,564 A | 5/1977 | Valiquette et al. |
| 4,340,063 A | 7/1982 | Maurer |
| 4,365,636 A | 12/1982 | Barker |
| 4,458,692 A | 7/1984 | Simson |
| 4,550,221 A | 10/1985 | Mabusth |
| 4,552,154 A | 11/1985 | Hartlaub |
| 4,562,841 A | 1/1986 | Brockway et al. |
| 4,573,481 A | 3/1986 | Bullara |
| 4,648,407 A | 3/1987 | Sackner |
| 4,680,708 A | 7/1987 | Ambos et al. |
| 4,686,332 A | 8/1987 | Greanias et al. |
| 4,827,935 A | 5/1989 | Geddes et al. |
| 4,860,766 A | 8/1989 | Sackner |
| 4,878,497 A | 11/1989 | Callaghan et al. |
| 4,928,688 A | 5/1990 | Mower |
| 4,953,551 A | 9/1990 | Mehra et al. |
| 4,979,507 A | 12/1990 | Heinz |
| 5,000,189 A | 3/1991 | Throne et al. |
| 5,033,467 A | 7/1991 | Bocchi et al. |
| 5,036,849 A | 8/1991 | Hauck et al. |
| 5,101,831 A | 4/1992 | Koyama et al. |
| 5,105,354 A | 4/1992 | Nishimura |
| 5,133,353 A | 7/1992 | Hauser |
| 5,146,918 A | 9/1992 | Kallok et al. |
| 5,170,784 A | 12/1992 | Ramon et al. |
| 5,178,156 A | 1/1993 | Takishima et al. |
| 5,179,945 A | 1/1993 | Van Hofwegen et al. |
| 5,184,615 A | 2/1993 | Nappholz et al. |
| 5,187,657 A | 2/1993 | Forbes |
| 5,203,348 A | 4/1993 | Dahl et al. |
| 5,209,229 A | 5/1993 | Gilli |
| 5,217,021 A | 6/1993 | Steinhaus et al. |
| 5,222,493 A | 6/1993 | Sholder |
| 5,230,337 A | 7/1993 | Dahl et al. |
| 5,233,983 A | 8/1993 | Markowitz |
| 5,261,400 A | 11/1993 | Bardy |
| 5,271,411 A | 12/1993 | Ripley et al. |
| 5,273,035 A | 12/1993 | Markowitz et al. |
| 5,284,136 A | 2/1994 | Hauck et al. |
| 5,292,338 A | 3/1994 | Bardy |
| 5,300,106 A | 4/1994 | Dahl et al. |
| 5,301,677 A | 4/1994 | Hsung |
| 5,313,953 A | 5/1994 | Yomtov et al. |
| 5,314,430 A | 5/1994 | Bardy |
| 5,314,459 A | 5/1994 | Swanson et al. |
| 5,318,597 A | 6/1994 | Hauck et al. |
| 5,324,310 A | 6/1994 | Greeninger et al. |
| 5,331,966 A | 7/1994 | Bennett et al. |
| 5,331,996 A | 7/1994 | Ziehm |
| 5,333,095 A | 7/1994 | Stevenson et al. |
| 5,334,222 A | 8/1994 | Salo et al. |
| 5,335,657 A | 8/1994 | Terry, Jr. et al. |
| 5,350,410 A | 9/1994 | Kleks et al. |
| 5,353,788 A | 10/1994 | Miles |
| 5,360,442 A | 11/1994 | Dahl et al. |
| 5,366,496 A | 11/1994 | Dahl et al. |
| 5,372,606 A | 12/1994 | Lang et al. |
| 5,374,280 A | 12/1994 | den Dulk |
| 5,376,106 A | 12/1994 | Stahmann et al. |
| 5,376,476 A | 12/1994 | Eylon |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,529 A | 5/1995 | Hudrlik |
| 5,411,533 A | 5/1995 | Dubreuil et al. |
| 5,411,539 A | 5/1995 | Neisz |
| 5,431,693 A | 7/1995 | Schroeppel |
| 5,439,482 A | 8/1995 | Adams et al. |
| 5,441,518 A | 8/1995 | Adams et al. |
| 5,443,485 A | 8/1995 | Housworth et al. |
| 5,447,519 A | 9/1995 | Peterson |
| 5,468,254 A | 11/1995 | Hahn et al. |
| 5,485,851 A | 1/1996 | Erickson |
| 5,517,983 A | 5/1996 | Deighan et al. |
| 5,520,191 A | 5/1996 | Karlsson et al. |
| 5,522,860 A | 6/1996 | Molin et al. |
| 5,531,779 A | 7/1996 | Dahl et al. |
| 5,534,017 A | 7/1996 | Van Krieken et al. |
| 5,540,727 A | 7/1996 | Tockman et al. |
| 5,540,732 A | 7/1996 | Testerman |
| 5,545,186 A | 8/1996 | Olson et al. |
| 5,545,202 A | 8/1996 | Dahl et al. |
| 5,549,655 A | 8/1996 | Erickson |
| 5,591,216 A | 1/1997 | Testerman et al. |
| 5,603,732 A | 2/1997 | Dahl et al. |
| 5,620,466 A | 4/1997 | Haefner et al. |
| 5,626,620 A | 5/1997 | Kieval et al. |
| 5,634,938 A | 6/1997 | Swanson et al. |
| 5,641,326 A | 6/1997 | Adams |
| 5,650,759 A | 7/1997 | Hittman et al. |
| 5,658,318 A | 8/1997 | Stroetmann et al. |
| 5,662,688 A | 9/1997 | Haefner et al. |
| 5,674,254 A | 10/1997 | van Krieken |
| 5,683,431 A | 11/1997 | Wang |
| 5,683,434 A | 11/1997 | Archer |
| 5,697,953 A | 12/1997 | Kroll et al. |
| 5,697,956 A | 12/1997 | Bornzin |
| 5,704,365 A | 1/1998 | Albrecht et al. |
| 5,713,933 A | 2/1998 | Condie et al. |
| 5,715,812 A | 2/1998 | Deighan et al. |
| 5,718,720 A | 2/1998 | Prutchi et al. |
| 5,724,984 A | 3/1998 | Arnold et al. |
| 5,735,883 A | 4/1998 | Paul et al. |
| 5,738,102 A | 4/1998 | Lemelson |
| 5,779,645 A | 7/1998 | Olson et al. |
| 5,814,087 A | 9/1998 | Renirie |
| 5,817,027 A | 10/1998 | Arand et al. |
| 5,827,326 A | 10/1998 | Kroll et al. |
| 5,836,987 A | 11/1998 | Baumann et al. |
| 5,844,506 A | 12/1998 | Binstead |
| 5,855,593 A | 1/1999 | Olson et al. |
| 5,857,977 A | 1/1999 | Caswell et al. |
| 5,860,918 A | 1/1999 | Schradi et al. |
| 5,861,011 A | 1/1999 | Stoop |
| 5,861,013 A | 1/1999 | Peck et al. |
| 5,871,512 A | 2/1999 | Hemming et al. |
| 5,873,898 A | 2/1999 | Hemming et al. |
| 5,876,353 A | 3/1999 | Riff |
| 5,895,414 A | 4/1999 | Sanchez-Zambrano |
| 5,916,243 A | 6/1999 | KenKnight et al. |
| 5,944,680 A | 8/1999 | Christopherson et al. |
| 5,957,956 A | 9/1999 | Kroll et al. |
| 5,964,778 A | 10/1999 | Fugoso et al. |
| 5,974,340 A | 10/1999 | Kadhiresan |
| 5,987,352 A | 11/1999 | Klein et al. |
| 6,026,320 A | 2/2000 | Carlson et al. |
| 6,038,474 A | 3/2000 | Zhu et al. |
| 6,044,298 A | 3/2000 | Salo et al. |
| 6,045,513 A | 4/2000 | Stone et al. |
| 6,049,730 A | 4/2000 | Kristbjarnarson |
| 6,052,620 A | 4/2000 | Gillberg et al. |
| 6,055,454 A | 4/2000 | Heemels |
| 6,064,910 A | 5/2000 | Andersson et al. |
| 6,076,014 A | 6/2000 | Alt |
| 6,076,015 A | 6/2000 | Hartley et al. |
| 6,084,253 A | 7/2000 | Turner, Jr. |
| 6,091,973 A | 7/2000 | Colla et al. |

(56) References Cited

U.S. PATENT DOCUMENTS

| | | |
|---|---|---|
| 6,101,416 A | 8/2000 | Sloman |
| 6,115,628 A | 9/2000 | Stadler et al. |
| 6,120,441 A | 9/2000 | Griebel |
| 6,126,611 A | 10/2000 | Bourgeois et al. |
| 6,128,534 A | 10/2000 | Park et al. |
| 6,128,535 A | 10/2000 | Maarse |
| 6,132,384 A | 10/2000 | Christopherson et al. |
| 6,134,473 A | 10/2000 | Hemming et al. |
| 6,141,581 A | 10/2000 | Olson et al. |
| 6,147,680 A | 11/2000 | Tareev |
| 6,148,230 A | 11/2000 | Kenknight |
| 6,148,234 A | 11/2000 | Struble |
| 6,163,724 A | 12/2000 | Hemming et al. |
| 6,169,921 B1 | 1/2001 | KenKnight et al. |
| 6,175,766 B1 | 1/2001 | Bornzin et al. |
| 6,190,326 B1 | 2/2001 | McKinnon et al. |
| 6,192,275 B1 | 2/2001 | Zhu et al. |
| 6,221,011 B1 | 4/2001 | Bardy |
| 6,226,551 B1 | 5/2001 | Zhu et al. |
| 6,227,072 B1 | 5/2001 | Ritchey et al. |
| 6,238,419 B1 | 5/2001 | Lindgren |
| 6,251,126 B1 | 6/2001 | Ottenhoff et al. |
| 6,253,102 B1 | 6/2001 | Hsu et al. |
| 6,258,039 B1 | 7/2001 | Okamoto et al. |
| 6,259,947 B1 | 7/2001 | Olson et al. |
| 6,266,554 B1 | 7/2001 | Hsu et al. |
| 6,270,457 B1 | 8/2001 | Bardy |
| 6,272,377 B1 | 8/2001 | Sweeney et al. |
| 6,275,731 B1 | 8/2001 | Zhu et al. |
| 6,277,072 B1 | 8/2001 | Bardy |
| 6,280,380 B1 | 8/2001 | Bardy |
| 6,280,462 B1 | 8/2001 | Hauser et al. |
| 6,282,440 B1 | 8/2001 | Brodnick et al. |
| 6,285,907 B1 | 9/2001 | Kramer et al. |
| 6,295,330 B1 | 9/2001 | Skog et al. |
| 6,299,581 B1 | 10/2001 | Rapoport |
| 6,312,378 B1 | 11/2001 | Bardy |
| 6,312,388 B1 | 11/2001 | Marcovecchio et al. |
| 6,324,421 B1 | 11/2001 | Stadler et al. |
| 6,324,427 B1 | 11/2001 | Florio |
| 6,336,903 B1 | 1/2002 | Bardy |
| 6,345,201 B1 | 2/2002 | Sloman et al. |
| 6,351,669 B1 | 2/2002 | Hartley et al. |
| 6,351,673 B1 | 2/2002 | Ding et al. |
| 6,353,759 B1 | 3/2002 | Hartley et al. |
| 6,358,203 B2 | 3/2002 | Bardy |
| 6,360,127 B1 | 3/2002 | Ding et al. |
| 6,363,270 B1 | 3/2002 | Colla et al. |
| 6,363,281 B1 | 3/2002 | Zhu et al. |
| 6,368,284 B1 | 4/2002 | Bardy |
| 6,368,287 B1 | 4/2002 | Hadas |
| 6,371,922 B1 | 4/2002 | Baumann et al. |
| 6,375,621 B1 | 4/2002 | Sullivan |
| 6,393,316 B1 | 5/2002 | Gillberg et al. |
| 6,398,728 B1 | 6/2002 | Bardy |
| 6,409,675 B1 | 6/2002 | Turcott |
| 6,411,848 B2 | 6/2002 | Kramer et al. |
| 6,415,174 B1 | 7/2002 | Bebehani et al. |
| 6,415,183 B1 | 7/2002 | Scheiner et al. |
| 6,418,340 B1 | 7/2002 | Conley et al. |
| 6,418,343 B1 | 7/2002 | Zhang et al. |
| 6,424,234 B1 | 7/2002 | Stevenson |
| 6,424,865 B1 | 7/2002 | Ding |
| 6,434,417 B1 | 8/2002 | Lovett |
| 6,434,428 B1 | 8/2002 | Sloman |
| 6,438,409 B1 | 8/2002 | Malik et al. |
| 6,438,410 B2 | 8/2002 | Hsu et al. |
| 6,440,066 B1 | 8/2002 | Bardy |
| 6,449,503 B1 | 9/2002 | Hsu |
| 6,456,481 B1 | 9/2002 | Stevenson |
| 6,456,880 B1 | 9/2002 | Park et al. |
| 6,456,881 B1 | 9/2002 | Bornzin |
| 6,459,929 B1 | 10/2002 | Hopper et al. |
| 6,466,820 B1 | 10/2002 | Juran et al. |
| 6,477,422 B1 | 11/2002 | Splett |
| 6,480,733 B1 | 11/2002 | Turcott |
| 6,480,734 B1 | 11/2002 | Zhang et al. |
| 6,487,443 B2 | 11/2002 | Olson et al. |
| 6,491,639 B1 | 12/2002 | Turcott |
| 6,493,586 B1 | 12/2002 | Stahmann et al. |
| 6,496,715 B1 | 12/2002 | Lee et al. |
| 6,505,067 B1 | 1/2003 | Lee et al. |
| 6,505,071 B1 | 1/2003 | Zhu et al. |
| 6,512,940 B1 | 1/2003 | Brabec et al. |
| 6,512,953 B2 | 1/2003 | Florio et al. |
| 6,522,915 B1 | 2/2003 | Ceballos et al. |
| 6,542,775 B2 | 4/2003 | Ding et al. |
| 6,553,259 B2 | 4/2003 | Mouchawar et al. |
| 6,564,106 B2 | 5/2003 | Guck et al. |
| 6,567,701 B2 | 5/2003 | Vonk |
| 6,574,507 B1 | 6/2003 | Bonnet |
| 6,589,188 B1 | 7/2003 | Street et al. |
| 6,595,927 B2 | 7/2003 | Pitts-Crick et al. |
| 6,597,951 B2 | 7/2003 | Kramer et al. |
| 6,600,949 B1 | 7/2003 | Turcott |
| 6,607,509 B2 | 8/2003 | Bobroff et al. |
| 6,611,712 B2 | 8/2003 | Spinelli et al. |
| 6,615,082 B1 | 9/2003 | Mandell et al. |
| 6,615,083 B2 | 9/2003 | Kupper |
| 6,615,089 B1 | 9/2003 | Russie et al. |
| 6,618,619 B1 | 9/2003 | Florio et al. |
| 6,622,046 B2 | 9/2003 | Fraley et al. |
| 6,631,290 B1 | 10/2003 | Guck et al. |
| 6,640,136 B1 | 10/2003 | Helland et al. |
| 6,641,542 B2 | 11/2003 | Cho et al. |
| 6,654,637 B2 | 11/2003 | Rouw et al. |
| 6,658,293 B2 | 12/2003 | Vonk |
| 6,684,100 B1 | 1/2004 | Sweeney et al. |
| 6,690,967 B2 | 2/2004 | Meij et al. |
| 6,701,170 B2 | 3/2004 | Stetson |
| 6,708,058 B2 | 3/2004 | Kim et al. |
| 6,725,085 B2 | 4/2004 | Schwartzman et al. |
| 6,731,973 B2 | 5/2004 | Voith et al. |
| 6,731,983 B2 | 5/2004 | Ericksen et al. |
| 6,731,984 B2 | 5/2004 | Cho et al. |
| 6,731,985 B2 | 5/2004 | Poore et al. |
| 6,738,668 B1 | 5/2004 | Mouchawar et al. |
| 6,738,669 B1 | 5/2004 | Sloman et al. |
| 6,754,523 B2 | 6/2004 | Toole |
| 6,754,528 B2 | 6/2004 | Bardy et al. |
| 6,760,615 B2 | 7/2004 | Ferek-Petric |
| 6,766,190 B2 | 7/2004 | Ferek-Petric |
| 6,768,923 B2 | 7/2004 | Ding et al. |
| 6,768,924 B2 | 7/2004 | Ding et al. |
| 6,772,008 B2 | 8/2004 | Zhu et al. |
| 6,773,404 B2 | 8/2004 | Poezevera |
| 6,778,860 B2 | 8/2004 | Ostroff et al. |
| 6,788,974 B2 | 9/2004 | Bardy et al. |
| 6,830,548 B2 | 12/2004 | Bonnet et al. |
| 6,834,204 B2 | 12/2004 | Ostroff et al. |
| 6,856,835 B2 | 2/2005 | Bardy et al. |
| 6,865,417 B2 | 3/2005 | Rissmann et al. |
| 6,866,044 B2 | 3/2005 | Bardy et al. |
| 6,881,192 B1 | 4/2005 | Park |
| 6,884,218 B2 | 4/2005 | Olson |
| 6,885,893 B1 | 4/2005 | Lu |
| 6,888,538 B2 | 5/2005 | Ely et al. |
| 6,889,079 B2 | 5/2005 | Bocek et al. |
| 6,890,306 B2 | 5/2005 | Poezevera et al. |
| 6,895,274 B2 | 5/2005 | Mower |
| 6,904,315 B2 | 6/2005 | Panken et al. |
| 6,904,320 B2 | 6/2005 | Park et al. |
| 6,915,160 B2 | 7/2005 | Auricchio et al. |
| 6,915,164 B2 | 7/2005 | Bradley et al. |
| 6,917,832 B2 | 7/2005 | Hutten et al. |
| 6,925,324 B2 | 8/2005 | Shusterman |
| 6,925,330 B2 | 8/2005 | Kleine |
| 6,927,721 B2 | 8/2005 | Ostroff |
| 6,928,324 B2 | 8/2005 | Park et al. |
| 6,937,907 B2 | 8/2005 | Bardy et al. |
| 6,944,495 B2 | 9/2005 | MacAdam et al. |
| 6,944,579 B2 | 9/2005 | Shimizu |
| 6,950,702 B2 | 9/2005 | Sweeney |
| 6,950,705 B2 | 9/2005 | Bardy et al. |

(56) References Cited

U.S. PATENT DOCUMENTS

| | | |
|---|---|---|
| 6,952,608 B2 | 10/2005 | Ostroff |
| 6,952,610 B2 | 10/2005 | Ostroff et al. |
| 6,954,670 B2 | 10/2005 | Ostroff |
| 6,959,214 B2 | 10/2005 | Pape et al. |
| 6,961,613 B2 | 11/2005 | Björling et al. |
| 6,961,619 B2 | 11/2005 | Casey |
| 6,973,350 B1 | 12/2005 | Levine et al. |
| 6,975,904 B1 | 12/2005 | Sloman |
| 6,978,178 B2 | 12/2005 | Sommer et al. |
| 6,983,264 B2 | 1/2006 | Shimizu |
| 6,988,003 B2 | 1/2006 | Bardy et al. |
| 6,993,379 B1 | 1/2006 | Kroll et al. |
| 6,993,389 B2 | 1/2006 | Ding et al. |
| 6,999,817 B2 | 2/2006 | Park et al. |
| 7,006,869 B2 | 2/2006 | Bradley et al. |
| 7,025,730 B2 | 4/2006 | Cho et al. |
| 7,027,861 B2 | 4/2006 | Thompson |
| 7,027,868 B2 | 4/2006 | Rueter et al. |
| 7,027,871 B2 | 4/2006 | Burnes et al. |
| 7,031,773 B1 | 4/2006 | Levine et al. |
| 7,039,459 B2 | 5/2006 | Bardy et al. |
| 7,039,465 B2 | 5/2006 | Bardy et al. |
| 7,043,299 B2 | 5/2006 | Erlinger et al. |
| 7,050,851 B2 | 5/2006 | Plombon et al. |
| 7,062,327 B2 | 6/2006 | Bradley et al. |
| 7,065,400 B2 | 6/2006 | Schechter |
| 7,065,407 B2 | 6/2006 | Bardy et al. |
| 7,065,410 B2 | 6/2006 | Bardy et al. |
| 7,069,080 B2 | 6/2006 | Bardy et al. |
| 7,076,296 B2 | 7/2006 | Bardy et al. |
| 7,079,988 B2 | 7/2006 | Albera et al. |
| 7,081,095 B2 | 7/2006 | Lynn et al. |
| 7,085,599 B2 | 8/2006 | Kim et al. |
| 7,090,682 B2 | 8/2006 | Sanders et al. |
| 7,092,754 B2 | 8/2006 | Bardy et al. |
| 7,094,207 B1 | 8/2006 | Koh |
| 7,096,064 B2 | 8/2006 | Deno et al. |
| 7,103,404 B2 | 9/2006 | Stadler et al. |
| 7,107,093 B2 | 9/2006 | Burnes |
| 7,113,823 B2 | 9/2006 | Yonce et al. |
| 7,115,097 B2 | 10/2006 | Johnson |
| 7,117,036 B2 | 10/2006 | Florio |
| 7,120,495 B2 | 10/2006 | Bardy et al. |
| 7,123,960 B2 | 10/2006 | Ding et al. |
| 7,127,290 B2 | 10/2006 | Girouard et al. |
| 7,129,935 B2 | 10/2006 | Mackey |
| 7,139,610 B2 | 11/2006 | Ferek-Petric |
| 7,144,586 B2 | 12/2006 | Levy et al. |
| 7,146,212 B2 | 12/2006 | Bardy et al. |
| 7,149,575 B2 | 12/2006 | Ostroff et al. |
| 7,155,278 B2 | 12/2006 | King et al. |
| 7,160,252 B2 | 1/2007 | Cho et al. |
| 7,177,689 B2 | 2/2007 | Ternes et al. |
| 7,179,229 B1 | 2/2007 | Koh |
| 7,181,285 B2 | 2/2007 | Lindh et al. |
| 7,184,825 B2 | 2/2007 | Leinsing et al. |
| 7,184,835 B2 | 2/2007 | Kramer et al. |
| 7,191,003 B2 | 3/2007 | Greenhut et al. |
| 7,191,004 B2 | 3/2007 | Kim et al. |
| 7,194,302 B2 | 3/2007 | Bardy et al. |
| 7,194,309 B2 | 3/2007 | Ostroff et al. |
| 7,194,313 B2 | 3/2007 | Libbus |
| 7,203,540 B2 | 4/2007 | Ding et al. |
| 7,203,542 B2 | 4/2007 | Obel et al. |
| 7,203,543 B2 | 4/2007 | Meyer et al. |
| 7,212,862 B2 | 5/2007 | Park et al. |
| 7,225,021 B1 | 5/2007 | Park |
| 7,228,173 B2 | 6/2007 | Cazares |
| 7,233,821 B2 | 6/2007 | Hettrick et al. |
| 7,236,819 B2 | 6/2007 | Brockway et al. |
| 7,242,978 B2 | 7/2007 | Cao et al. |
| 7,245,962 B2 | 7/2007 | Ciaccio et al. |
| 7,248,921 B2 | 7/2007 | Palreddy et al. |
| 7,248,925 B2 | 7/2007 | Bruhns et al. |
| 7,263,399 B2 | 8/2007 | Carlson |
| 7,277,754 B2 | 10/2007 | McCabe et al. |
| 7,286,876 B2 | 10/2007 | Yonce et al. |
| 7,299,086 B2 | 11/2007 | McCabe et al. |
| 7,299,093 B2 | 11/2007 | Zhu et al. |
| 7,308,311 B2 | 12/2007 | Sorensen et al. |
| 7,319,900 B2 | 1/2008 | Kim et al. |
| 7,330,761 B2 | 2/2008 | Zhang |
| 7,337,000 B2 | 2/2008 | Meyer et al. |
| 7,359,749 B2 | 4/2008 | Quenet et al. |
| 7,369,889 B2 | 5/2008 | Aström et al. |
| 7,392,086 B2 | 6/2008 | Sathaye |
| 7,426,412 B1 | 9/2008 | Schecter |
| 7,438,686 B2 | 10/2008 | Cho |
| 7,457,664 B2 | 11/2008 | Zhang et al. |
| 7,468,040 B2 | 12/2008 | Hartley |
| 7,477,932 B2 | 1/2009 | Lee et al. |
| 7,499,751 B2 | 3/2009 | Meyer et al. |
| 7,509,170 B2 | 3/2009 | Zhang et al. |
| 7,587,240 B2 | 9/2009 | Zhang et al. |
| 7,617,002 B2 | 11/2009 | Goetz |
| 7,647,108 B2 | 1/2010 | Freeberg |
| 7,680,536 B2 | 3/2010 | Sathaye et al. |
| 7,684,861 B2 | 3/2010 | Sanders |
| 7,734,347 B2 | 6/2010 | Sathaye et al. |
| 7,738,959 B2 | 6/2010 | Manrodt et al. |
| 7,774,064 B2 | 8/2010 | Meyer et al. |
| 9,993,205 B2 * | 6/2018 | Meyer .................. A61N 1/371 |
| 2001/0049542 A1 | 12/2001 | Florio et al. |
| 2002/0002327 A1 | 1/2002 | Grant et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035381 A1 | 3/2002 | Bardy et al. |
| 2002/0052631 A1 | 5/2002 | Sullivan et al. |
| 2002/0082658 A1 | 6/2002 | Heinrich et al. |
| 2002/0095184 A1 | 7/2002 | Bardy et al. |
| 2002/0107544 A1 | 8/2002 | Ostroff et al. |
| 2002/0107545 A1 | 8/2002 | Rissmann et al. |
| 2002/0138111 A1 | 9/2002 | Greenhut et al. |
| 2003/0023175 A1 | 1/2003 | Arzbaecher et al. |
| 2003/0050671 A1 | 3/2003 | Bradley |
| 2003/0083710 A1 | 5/2003 | Ternes et al. |
| 2003/0083711 A1 | 5/2003 | Yonce et al. |
| 2003/0135248 A1 | 7/2003 | Stypulkowski |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2003/0212436 A1 | 11/2003 | Brown |
| 2004/0116978 A1 | 6/2004 | Bradley |
| 2004/0127950 A1 | 7/2004 | Kim et al. |
| 2004/0172065 A1 | 9/2004 | Sih et al. |
| 2004/0215253 A1 | 10/2004 | Weinberg |
| 2004/0215277 A1 | 10/2004 | Oosterhoff et al. |
| 2004/0230229 A1 | 11/2004 | Lovett et al. |
| 2004/0243014 A1 | 12/2004 | Lee et al. |
| 2004/0260351 A1 | 12/2004 | Holmstrom et al. |
| 2005/0004612 A1 | 1/2005 | Scholten et al. |
| 2005/0010120 A1 | 1/2005 | Jung et al. |
| 2005/0038478 A1 | 2/2005 | Klepfer et al. |
| 2005/0043652 A1 | 2/2005 | Lovett et al. |
| 2005/0065587 A1 | 3/2005 | Gryzwa |
| 2005/0085865 A1 | 4/2005 | Tehrani |
| 2005/0107839 A1 | 5/2005 | Sanders |
| 2005/0113710 A1 | 5/2005 | Stahmann et al. |
| 2005/0131477 A1 | 6/2005 | Meyer |
| 2005/0131478 A1 | 6/2005 | Kim et al. |
| 2005/0288600 A1 | 12/2005 | Zhang et al. |
| 2006/0069322 A1 | 3/2006 | Zhang et al. |
| 2006/0074331 A1 | 4/2006 | Kim et al. |
| 2006/0111747 A1 | 5/2006 | Cazares et al. |
| 2006/0116593 A1 | 6/2006 | Zhang et al. |
| 2006/0129193 A1 | 6/2006 | Zhang |
| 2006/0129194 A1 | 6/2006 | Zhang |
| 2006/0129196 A1 | 6/2006 | Dong et al. |
| 2006/0129199 A1 | 6/2006 | Zhang et al. |
| 2006/0241706 A1 | 10/2006 | Yonce et al. |
| 2006/0247693 A1 | 11/2006 | Dong et al. |
| 2006/0247695 A1 | 11/2006 | Stalsberg et al. |
| 2006/0253043 A1 | 11/2006 | Zhang et al. |

(56) References Cited

U.S. PATENT DOCUMENTS

| | | |
|---|---|---|
| 2006/0253044 A1 | 11/2006 | Zhang |
| 2007/0049974 A1 | 3/2007 | Li et al. |
| 2007/0055124 A1 | 3/2007 | Viswanathan et al. |
| 2007/0142737 A1 | 6/2007 | Cazares et al. |
| 2007/0142741 A1 | 6/2007 | Berthon-jones et al. |
| 2007/0239057 A1 | 10/2007 | Pu et al. |
| 2007/0255321 A1 | 11/2007 | Gerber et al. |
| 2008/0004665 A1 | 1/2008 | McCabe et al. |
| 2008/0009909 A1 | 1/2008 | Sathaye et al. |
| 2008/0045851 A1 | 2/2008 | Cazares et al. |
| 2008/0071318 A1 | 3/2008 | Brooke et al. |
| 2008/0275522 A1 | 11/2008 | Dong et al. |
| 2008/0294215 A1 | 11/2008 | Sathaye |
| 2008/0300644 A1 | 12/2008 | Sathaye |
| 2009/0030470 A1 | 1/2009 | Holmstrom et al. |
| 2009/0043351 A1 | 2/2009 | Sathaye et al. |
| 2009/0043352 A1 | 2/2009 | Brooke et al. |
| 2010/0256703 A1 | 10/2010 | Meyer et al. |

FOREIGN PATENT DOCUMENTS

| | | |
|---|---|---|
| EP | 0940155 A3 | 9/1999 |
| EP | 1038498 A2 | 9/2000 |
| EP | 1151718 A3 | 9/2002 |
| EP | 1291038 A2 | 3/2003 |
| EP | 1629863 A1 | 3/2006 |
| WO | WO-92017240 A1 | 10/1992 |
| WO | WO-92020402 A1 | 11/1992 |
| WO | WO-99004841 A1 | 2/1999 |
| WO | WO-0001438 A1 | 1/2000 |
| WO | WO-00017615 A2 | 3/2000 |
| WO | WO-0240097 A1 | 5/2002 |
| WO | WO 0247761 A2 | 6/2002 |
| WO | WO-02087696 A1 | 11/2002 |
| WO | WO-03003905 A2 | 1/2003 |
| WO | WO-03028550 A2 | 4/2003 |
| WO | WO-2004026398 A1 | 4/2004 |
| WO | WO-2004091720 A2 | 10/2004 |
| WO | WO-2005058412 A2 | 6/2005 |
| WO | WO-2005089865 A1 | 9/2005 |
| WO | WO-2006065707 A2 | 6/2006 |
| WO | WO-2007087025 A1 | 8/2007 |
| WO | WO-2008005270 A2 | 1/2008 |
| WO | WO-2009020639 A1 | 2/2009 |

OTHER PUBLICATIONS

"U.S. Appl. No. 10/734,599, Examiner Interview Summary dated Sep. 18, 2009", 2 pgs.

"U.S. Appl. No. 10/734,599, Examiner Interview Summary dated Dec. 8, 2009", 3 pgs.

"U.S. Appl. No. 10/734,599, Final Office Action dated Dec. 6, 2007", 9 pgs.

"U.S. Appl. No. 10/734,599, Non Final Office Action dated Feb. 7, 2006", 14 pgs.

"U.S. Appl. No. 10/734,599, Non Final Office Action dated Mar. 18, 2009", 10 pgs.

"U.S. Appl. No. 10/734,599, Non Final Office Action dated Sep. 21, 2006", 8 pgs.

"U.S. Appl. No. 10/734,599, Non Final Office Action dated Sep. 21, 2009", 7 pgs.

"U.S. Appl. No. 10/734,599, Notice of Allowance dated Mar. 19, 2010", 4 pgs.

"U.S. Appl. No. 10/734,599, Preliminary Amendment filed Apr. 6, 2004", 12 pgs.

"U.S. Appl. No. 10/734,599, PTO Response to Rule 312 Communication dated Jul. 15, 2010", 2 pgs.

"U.S. Appl. No. 10/734,599, Reposnse filed Dec. 21, 2009 to Non Final Office Action dated Sep. 21, 2009", 14 pgs.

"U.S. Appl. No. 10/734,599, Reposnse filed Jan. 25, 2007 to Non Final Office Action dated Sep. 21, 2006", 16 pgs.

"U.S. Appl. No. 10/734,599, Response filed Feb. 11, 2008 to Final Office Action dated Dec. 6, 2007", 16 pgs.

"U.S. Appl. No. 10/734,599, Response filed Jun. 7, 2006 to Non Final Office Action dated Feb. 7, 2006", 20 pgs.

"U.S. Appl. No. 10/734,599, Response filed Jun. 9, 2009 to Non Final Office Action dated Mar. 18, 2009", 14 pgs.

"U.S. Appl. No. 10/734,599, Response filed Sep. 22, 2008 to Final Office Action dated Dec. 6, 2007", 15 pgs.

"U.S. Appl. No. 11/116,558, Advisory Action dated May 28, 2008", 3 pgs.

"U.S. Appl. No. 11/116,558, Final Office Action dated Mar. 6, 2008", 14 pgs.

"U.S. Appl. No. 11/116,558, Non Final Office Action dated Mar. 28, 2007", 12 pgs.

"U.S. Appl. No. 11/116,558, Response filed May 5, 2008 to Final Office Action dated Mar. 6, 2008", 11 pgs.

"U.S. Appl. No. 11/116,558, Response filed Sep. 28, 2007 to Non Final Office Action dated Mar. 28, 2007", 15 pgs.

"U.S. Appl. No. 11/116,558, Response filed Oct. 26, 2007 to Notice of Non-Compliant Amendment dated Oct. 15, 2007", 7 pgs.

"U.S. Appl. No. 12/818,066, Advisory Action dated May 21, 2013", 3 pgs.

"U.S. Appl. No. 12/818,066, Advisory Action dated Jul. 21, 2014", 4 pgs.

"U.S. Appl. No. 12/818,066, Appeal Brief mailed Sep. 29, 2014", 43 pgs.

"U.S. Appl. No. 12/818,066, Appeal Decision mailed Feb. 28, 2017", 8 pgs.

"U.S. Appl. No. 12/818,066, Decision on Pre-Appeal Brief mailed Jun. 27, 2013", 2 pgs.

"U.S. Appl. No. 12/818,066, Decision on Pre-Appeal Brief mailed Aug. 27, 2014", 2 pgs.

"U.S. Appl. No. 12/818,066, Examiner Interview Summary dated Mar. 14, 2013", 3 pgs.

"U.S. Appl. No. 12/818,066, Examiner's Answer to Appeal Brief dated Mar. 11, 2015", 16 pgs.

"U.S. Appl. No. 12/818,066, Final Office Action dated Jan. 17, 2013", 10 pgs.

"U.S. Appl. No. 12/818,066, Final Office Action dated Apr. 17, 2014", 16 pgs.

"U.S. Appl. No. 12/818,066, Non Final Office Action dated Mar. 26, 2012", 10 pgs.

"U.S. Appl. No. 12/818,066, Non Final Office Action dated Aug. 14, 2013", 11 pgs.

"U.S. Appl. No. 12/818,066, Notice of Allowance dated Feb. 15, 2018", 5 pgs.

"U.S. Appl. No. 12/818,066, Notice of Allowance dated Jun. 7, 2017", 5 pgs.

"U.S. Appl. No. 12/818,066, Pre-Appeal Brief Request filed May 17, 2013", 6 pgs.

"U.S. Appl. No. 12/818,066, Pre-Appeal Brief Request filed Jul. 17, 2014", 7 pgs.

"U.S. Appl. No. 12/818,066, Preliminary Amendment filed Sep. 29, 2010", 7 pgs.

"U.S. Appl. No. 12/818,066, Reply Brief filed Apr. 30, 2015", 5 pgs.

"U.S. Appl. No. 12/818,066, Response filed Apr. 11, 2013 to Final Office Action dated Jan. 17, 2013", 15 pgs.

"U.S. Appl. No. 12/818,066, Response filed Jun. 17, 2014 to Final Office Action dated Apr. 17, 2014", 30 pgs.

"U.S. Appl. No. 12/818,066, Response filed Jun. 26, 2012 to Non Final Office Action dated Mar. 26, 2012", 11 pgs.

"U.S. Appl. No. 12/818,066, Response filed Jul. 26, 2013 to Advisory Action dated May 21, 2013", 20 pgs.

"U.S. Appl. No. 12/818,066, Response filed Nov. 13, 2013 to Non Final Office Action dated Aug. 14, 2013", 19 pgs.

"File History for U.S. Appl. No. 12/217,652".

Acar, B., et al., "SVD-based on-line exercise ECG signal orthogonalization", IEEE Transactions on Biomedical Engineering, vol. 46, No. 3, (Mar. 1999), 311-32.

Ajiilore, O, et al., "Nightcap: Laboratory and home-based evaluation of a portable sleep monitor", Psychophysiology, 32, Abstract only, (1995), 1 pg.

(56) References Cited

OTHER PUBLICATIONS

Belouchrani, Adel, et al., "Blind Source Separation Based on Time-Frequency Signal Representations", IEEE Transactions on Signal Processing, vol. 46, No. 11, (Nov. 1998), 2888-2897.
Cohen, et al., "Capture Management Efficacy in children and young adults with endocardial and unipolar epicardial systems", Europace, vol. 6, (2004), 248-255.
Comon, Pierre, "Independent Component Analysis, A New Concept?", Signal Processing, vol. 36, No. 3, (Apr. 1994), 287-314.
Gallois, Philippe, et al., "Multi-Channel Analysis of the EEG Signals and Statistic Particularities for Epileptic Seizure Forecast", Second Joint EMBS/BMES Conference, (Oct. 2002), 208-215.
Gradaus, Rainer, et al., "Nonthoracotomy Implantable Cardioverter Defibrillator Placement in Children: Use of Subcutaneous Array Leads and Abdominally Placed Implantable Cardioverter Defibrillators in Children", Journal of Cardiovascular Electrophysiology, 12(3), (Mar. 2001), 356-360.
Hartz, Renee, et al., "New Approach to Defibrillator Insertion", J. Thoracic Cardiovascular Surgery, vol. 97, (1989), 920-922.
Hyvarinen, A, et al., "Independent Component Analysis: A Tutorial", Helsinski Univ. of Technology, (Apr. 1999).
Kolettis, Theofilos M, et al., "Submammary Implantation of a Cardioverter-Defibrillator with a Nonthoractorny Lead System", Am. Heart J., vol. 126, (Nov. 1993), 1222-1223.
Krahn, A. D, et al., "Recurrent Syncope. Experience with an Implantable Loop Record", Cardiol. Clin., vol. 15, No. 2, (May 1997), 316-326.
Leng, Charles T, et al., "Lead Configuration for Defibrillator Implantation in a Patient with Congenital Heart Disease and a Mechanical Prosthetic Tricuspid Valve", Pace, 24(8), (Aug. 2001), 1291-1292.
Park, et al., "Use of an Implantable Cardioverter Defibrillator in an Eight-Month-Old Infant with Ventricular Fibrillation Arising from a Myocardial Fibroma", Pace, 22(1), (Jan. 1999), 138-139.
Rieta, J. J, et al., "Atrial Activity Extraction Based on Blind Source Separation as an Alternative to QRST Cancellation for Atrial Fibrillation Analysis", Computers in Cardiology, vol. 27, (2000), 69-72.
Schuder, John C, et al., "Experimental Ventricular Defibrillation with an Automatic and Completely Implanted System", Trans. Am. Soc. Artif. Int. Organs, vol. 16, (1970), 207-212.
Schuder, John C, et al., "Transthoracic Ventricular Defibrillation in the Dog with Truncated and Untruncated Exponential Stimuli", IEEE Trans. on Bio-Medical Engin., vol. BME-18, No. 6, (Nov. 1971), 410-415.
Schuder, John C, et al., "Ventricular Defibrillation in the Dog using Implanted and Partially Implanted Electrode Systems", Am. J. of Cardiology, vol. 33, (Feb. 1974), 243-247.
Smits, et al., "Defibrillation Threshold (DFT) Model of a Fully Subcutaneous ICD System", Eurospace Supplements, vol. 2, (Jun. 2001), B83.
Splett, V., et al., "Determination of pacing capture in implantable defibrillators: benefit of evoked response detection using RV coil to can vector", Pacing Clin Electrophysiol., 23(11 Pt 1), (Nov. 2000), 1645-50.
Stirbis, P., et al., "Optimizing the Shape of Implanted Artificial Pacemakers", Kaunas Medical Institute. Translated from Meditsinskaya Tekhnika, No. 6, (1986), 25-27.
Verrier, et al., "Sleep Related Cardiovascular Risk: New Home-Based Monitoring Technology for Improved Diagnosis and Therapy", A.N.E., 2, (1997), 158-175.
Verrier, et al., "Sleep, dreams, and sudden death: the case for sleep as an autonomic stress test for the heart", Cardiovascular Research, 31, (1996), 181-211.
Waldemark, "Detection of Apnea Using Short Window FFT Technique and Artificial Neural Network", SPIE, International Society for Optical Engineering, vol. 3390, (1998), 122-133.
Zarzoso, Vicente, et al., "Blind Separation of Independent Sources for Virtually Any Probability Density Function", IEEE Transactions on Signal Processing, vol. 47, No. 9, (Sep. 1999), 2419-2432.
Zarzoso, Vicente, et al., "Noninvasive Fetal Electrocardiogram Extraction: Blind Separation Versus Adaptive Noise Cancellation", IEEE Transactions on Biomedical Engineering, vol. 48, No. 1, (Jan. 2001), 12-18.

\* cited by examiner

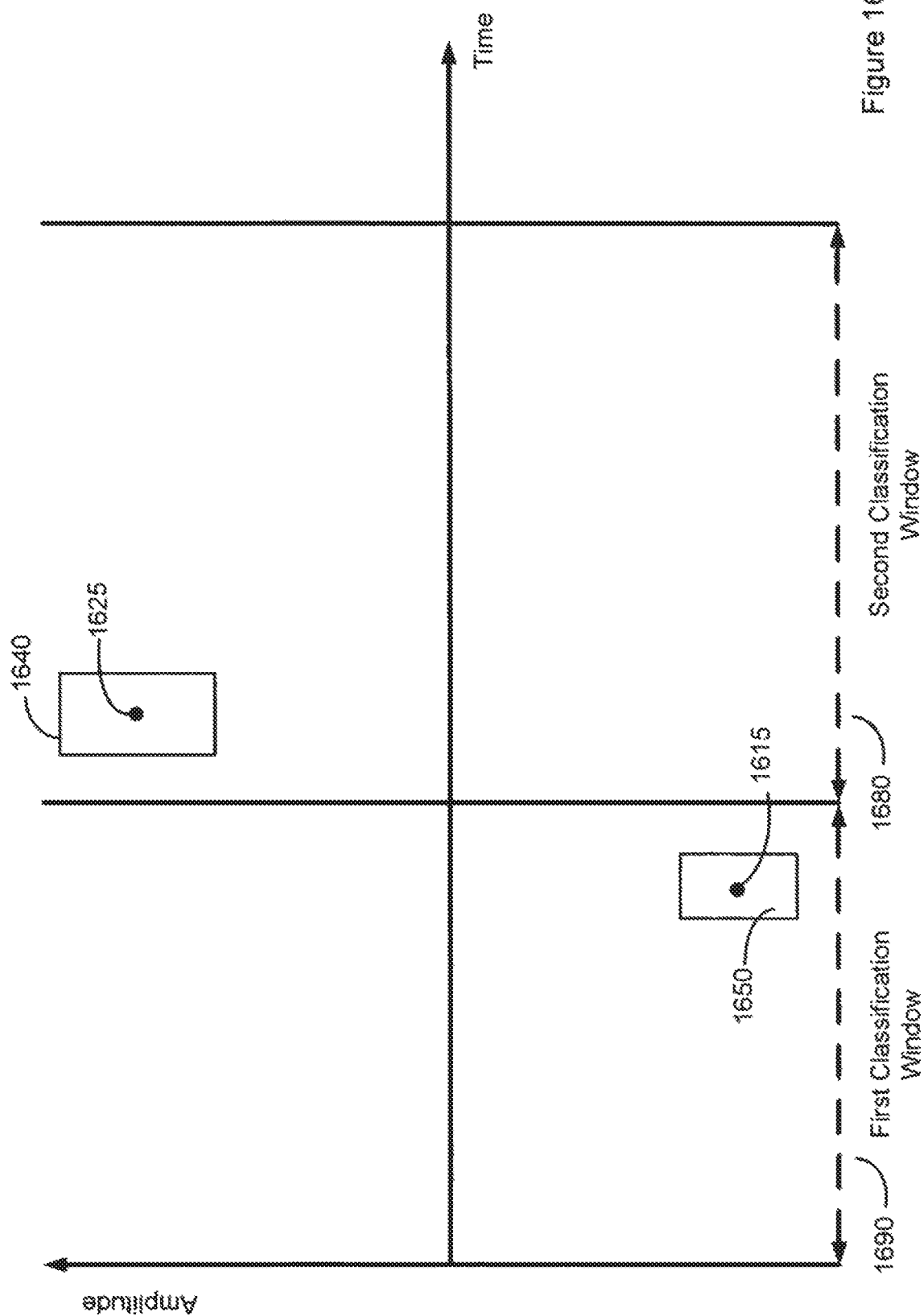

CARDIAC RESPONSE CLASSIFICATION USING RETRIGGERABLE CLASSIFICATION WINDOWS

RELATED PATENT DOCUMENTS

This patent application is a continuation of U.S. patent application Ser. No. 12/818,066 filed on Jun. 17, 2010, which is a continuation of U.S. patent application Ser. No. 10/734,599 filed on Dec. 12, 2003, now issued as U.S. Pat. No. 7,774,064, to which priority is claimed under 35 U.S.C. § 120, and each of which is incorporated herein by reference in its entirety.

FIELD OF THE INVENTION

The present invention relates generally to implantable medical devices and, more particularly, to classifying a cardiac response following delivery of a pace pulse.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically comprise circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal preceding the contraction is denoted the captured response (CR). The captured response may include an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Capture detection allows the cardiac rhythm management system to adjust the energy level of pace pulses to correspond to the optimum energy expenditure that reliably produces a contraction. Further, capture detection allows the cardiac rhythm management system to initiate a back-up pulse at a higher energy level whenever a pace pulse does not produce a contraction.

At times, a pacing pulse may merge with an intrinsic beat, producing a fusion beat. A fusion beat is a cardiac contraction that occurs when two cardiac depolarizations of a particular chamber, but from separate initiation sites, merge. When the heart is being paced, a fusion beat occurs when two cardiac depolarizations of a particular chamber, but from separate sites, merge. Fusion beats, as seen on electrocardiographic recordings, exhibit various morphologies. The merging depolarizations of a fusion beat do not contribute evenly to the total depolarization.

Pseudofusion occurs when a pacing stimulus is delivered on a spontaneous P wave during atrial pacing or on a spontaneous QRS complex during ventricular pacing. In pseudofusion, the pacing stimulus may be ineffective because the tissue around the electrode has already spontaneously depolarized and is in its refractory period.

During normal pacing, fusion/pseudofusion beats may be of little consequence except for wasted energy due to the generation of unnecessary pace pulses. However, discrimination between a fusion/pseudofusion beat and a captured response may be required during an automatic capture or threshold determination procedures. Fusion/pseudofusion beats may cause false detection of capture and may lead to erroneous capture threshold values and/or erroneous automatic capture verification information.

SUMMARY OF THE INVENTION

The present invention involves various methods and devices for classifying cardiac responses to pacing stimulation. In accordance with one embodiment of the invention, a method of classifying a cardiac response to a pacing stimulation involves delivering a pacing stimulation to a heart and establishing a first classification window subsequent to delivery of the pacing stimulation. A cardiac signal is sensed in the first classification window. A second classification window is established if a trigger characteristic of the cardiac signal is detected in the first classification window. The cardiac signal is sensed in the second classification window if the second classification window is triggered. The cardiac response to the pacing stimulation is classified based on one or more characteristics of the cardiac signal.

In accordance with another embodiment of the invention, a medical device includes a pulse delivery system and a sensing system. The pulse delivery system is configured to deliver a pacing stimulation to a heart. The sensing system is configured to a sense cardiac signal following delivery of the pacing stimulation. The medical device further includes a control system, coupled to the sensing system. The control system is configured to establish a first classification window subsequent to delivery of the pacing stimulation. The control system establishes a second classification window if a trigger characteristic of the cardiac signal is detected in the first classification window. The cardiac response to the pacing stimulation is classified by the control system based on one or more characteristics of the sensed cardiac signal.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 16B illustrates an averaged coordinate location of the cardiac signal peaks detected in the first cardiac response classification window in accordance with embodiments of the invention; and FIGS. 117A-17D are diagrams illustrating adjustment of a detection region in accordance with embodiments of the invention.

Figure 1:
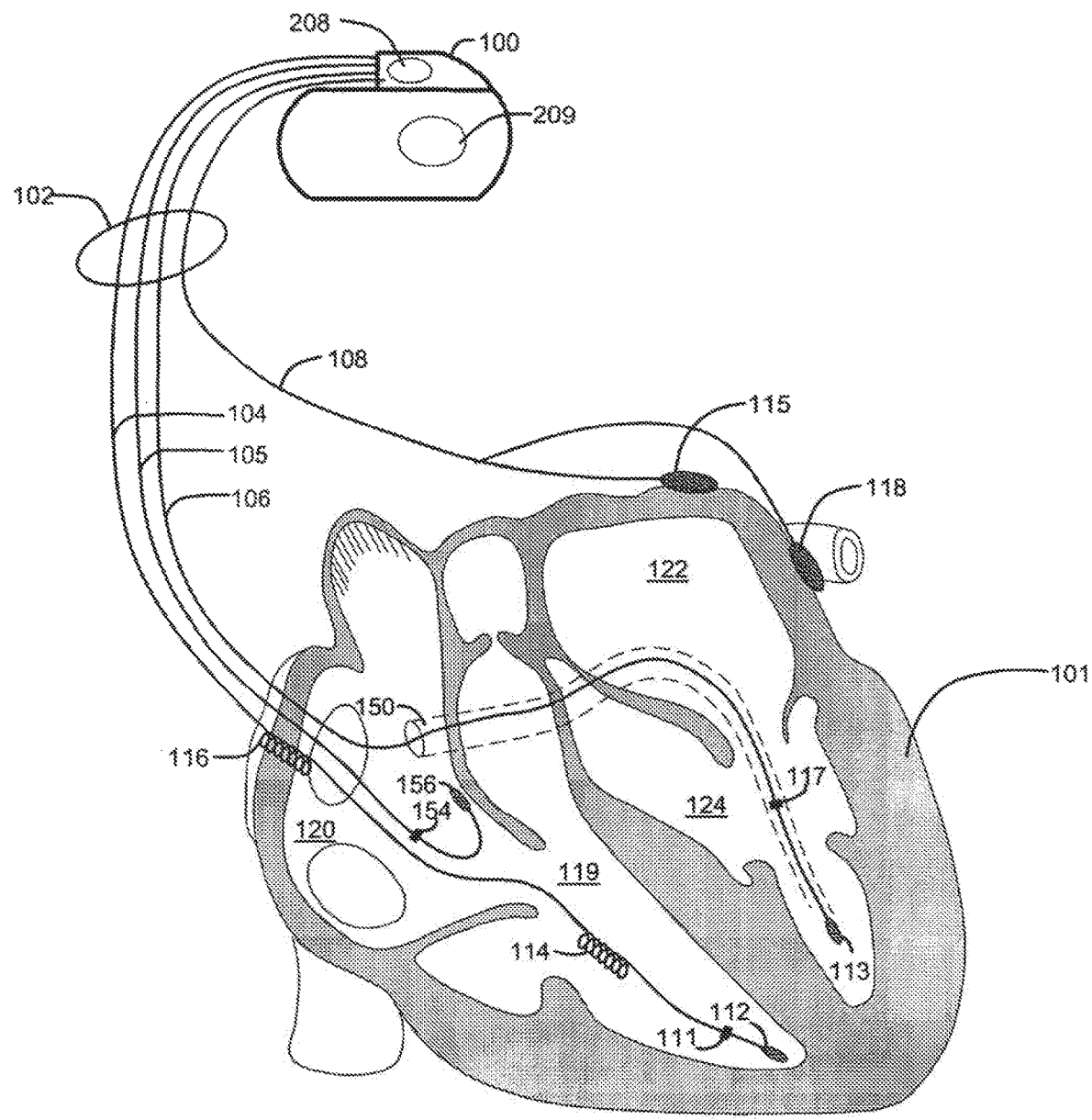
FIG. 1 is a partial view of one embodiment of an implantable medical device in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Embodiments of the invention are directed methods and systems for classifying the cardiac response following the delivery of pacing stimulation to the heart. In accordance with various aspects of the invention, cardiac response classification may be implemented by defining one or more retriggerable classification windows relative to and following a pacing stimulation.

In one approach, a first cardiac response classification window is established subsequent to a pacing pulse. A cardiac signal following the pacing stimulation is sensed in the first classification window. A second cardiac response classification is triggered if a trigger characteristic is detected in the first classification window, The cardiac response to the pacing stimulation is determined based on the one or more detected characteristics and the particular classification windows in which the one or more characteristics are detected. The cardiac response may be determined to be one of a captured response, a non-captured response, a non-captured response added to an intrinsic beat, and a fusion/pseudofusion beat, for example.

In another approach, multiple cardiac response classification windows may be triggered by characteristics of the cardiac signal. In one implementation, multiple classification windows may be triggered to allow the system to acquire additional information before classifying the cardiac response. In another implementation, additional classification windows may be triggered if non-capture is detected and a back up pace is delivered. In this situation, additional classification windows may be triggered to classify the cardiac response to the back up pace.

Various embodiments of the invention involve using the same electrode combination for pacing and sensing. Other embodiments involve using an electrode combination for pacing that is different from the electrode combination used for sensing the cardiac response to pacing. Employing different electrode combinations for pacing and sensing reduces the effect of the pacing artifact in the captured response signal.

By way of example, the processes of the present invention may be used to enhance capture threshold testing to determine the optimal energy for pacing. Determination of the optimal pacing energy may be implemented, for example, by an automatic capture threshold testing procedure executed by an implantable cardiac rhythm management system. Additionally, automatic capture verification may be used to monitor pacing on a beat-by-beat basis. Automatic capture verification may be used to control back up pacing when a pace pulse delivered to the heart fails to evoke a captured response (CR). These and other applications may be enhanced by employment of the systems and methods of the present invention.

Those skilled in the art will appreciate that reference to a capture threshold procedure indicates a method of determining the capture threshold in one of the left atrium, the right atrium, the left ventricle, and the right ventricle. In such a procedure, the pacemaker, automatically or upon command, initiates a search for the capture threshold of the selected heart chamber or chambers. The capture threshold is defined as the lowest pacing energy that consistently produces a contraction of the heart chamber.

In one example of an automatic capture threshold procedure, the pacemaker delivers a sequence of pacing pulses to the heart and detects the cardiac responses to the pace pulses. The energy of the pacing pulses may be decreased in discrete steps until a predetermined number of loss-of-capture events occur. After the predetermined number of loss-of-capture events occur, the pacemaker may increase the stimulation energy in discrete steps until a predetermined number of capture events occur to confirm the capture threshold. A capture threshold test may be performed using cardiac response classification methods of the present invention.

Other procedures for implementing capture threshold testing may be utilized. In one example, the pacing energy may be increased in discrete steps until capture is detected. In another example, the pacing energy may be adjusted according to a binomial search pattern.

Automatic capture threshold determination is distinguishable from automatic capture detection, a procedure that may occur on a beat-by-beat basis during pacing. Automatic capture detection verifies that a delivered pace pulse results in a captured response. When a captured response is not detected following a pace pulse, the pacemaker may deliver a back up safety pace to ensure consistent pacing. The back up pace may be delivered, for example, about 90-110 ms after the initial pace pulse. If a predetermined number of pace pulses delivered during normal pacing do not produce a captured response, the pacemaker may initiate a capture threshold test to determine the capture threshold. Automatic capture detection and back up pacing may be implemented using the cardiac response classification processes of the present invention.

The embodiments of the present system illustrated herein are generally described as being implemented in an implantable cardiac defibrillator (ICD) that may operate in numerous pacing modes known in the art. Various types of single and multiple chamber implantable cardiac defibrillators are known in the art and may be used in connection with the cardiac response classification methods of the present invention. The methods of the present invention may also be implemented a variety of implantable or patient-external cardiac rhythm management devices, including single and multi chamber pacemakers, defibrillators, cardioverters, bi-ventricular pacemakers, cardiac resynchronizers, and cardiac monitoring systems, for example.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

Referring now to FIG. 1 of the drawings, there is shown a cardiac rhythm management system that may be used to implement cardiac response classification methods of the present invention. The cardiac rhythm management system in FIG. 1 includes an ICD 100 electrically and physically coupled to a lead system 102. The housing and/or header of the ICD 100 may incorporate one or more electrodes 208, 209 used to provide electrical stimulation energy to the heart and to sense cardiac electrical activity. The ICD 100 may utilize all or a portion of the ICD housing as a can electrode 209. The ICD 100 may include an indifferent electrode positioned, for example, on the header or the housing of the ICD 100. If the ICD 100 includes both a can electrode 209 and an indifferent electrode 208, the electrodes 208, 209 typically are electrically isolated from each other.

The lead system 102 is used to detect electric cardiac signals produced by the heart 101 and to provide electrical energy to the heart 101 under certain predetermined conditions to treat cardiac arrhythmias. The lead system 102 may include one or more electrodes used for pacing, sensing, and/or defibrillation. In the embodiment shown in FIG. 1, the lead system 102 includes an intracardiac right ventricular (RV) lead system 104, an intracardiac right atrial (RA) lead system 105, an intracardiac left ventricular (LV) lead system 106, and an extracardiac left atrial (LA) lead system 108. The lead system 102 of FIG. 1 illustrates one embodiment that may be used in connection with the cardiac response classification methodologies described herein. Other leads and/or electrodes may additionally or alternatively be used.

The lead system 102 may include intracardiac leads 104, 105, 106 implanted in a human body with portions of the intracardiac leads 104, 105, 106 inserted into a heart 101. The intracardiac leads 104, 105, 106 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 1, the lead system 102 may include one or more extracardiac leads 108 having electrodes, e.g., epicardial electrodes, positioned at locations outside the heart for sensing and pacing one or more heart chambers.

The right ventricular lead system 104 illustrated in FIG. 1 includes an SVC-coil 116, an RV-coil 114, an RV-ring electrode 111, and an RV-tip electrode 112. The right ventricular lead system 104 extends through the right atrium 120 and into the right ventricle 119. In particular, the RV-tip electrode 112, RV-ring electrode 111, and RV-coil electrode 114 are positioned at appropriate locations within the right ventricle 119 for sensing and delivering electrical stimulation pulses to the heart. The SVC-coil 116 is positioned at an appropriate location within the right atrium chamber 120 of the heart 101 or a major vein leading to the right atrial chamber 120 of the heart 101.

In one configuration, the RV-tip electrode 112 referenced to the can electrode 209 may be used to implement unipolar pacing and/or sensing in the right ventricle 119. Bipolar pacing and/or sensing in the right ventricle may be implemented using the RV-tip 112 and RV-ring 111 electrodes. In yet another configuration, the RV-ring 111 electrode may optionally be omitted, and bipolar pacing and/or sensing may be accomplished using the RV-tip electrode 112 and the RV-coil 114, for example. The right ventricular lead system 104 may be configured as an integrated bipolar pace/shock lead. The RV-coil 114 and the SVC-coil 116 are defibrillation electrodes.

The left ventricular lead 106 includes an LV distal electrode 113 and an LV proximal electrode 117 located at appropriate locations in or about the left ventricle 124 for pacing and/or sensing the left ventricle 124. The left ventricular lead 106 may be guided into the right atrium 120 of the heart via the superior vena cava. From the right atrium 120, the left ventricular lead 106 may be deployed into the coronary sinus ostium, the opening of the coronary sinus 150. The lead 106 may be guided through the coronary sinus 150 to a coronary vein of the left ventricle 124. This vein is used as an access pathway for leads to reach the surfaces of the left ventricle 124 which are not directly accessible from the right side of the heart. Lead placement for the left ventricular lead 106 may be achieved via subclavian vein access and a preformed guiding catheter for insertion of the LV electrodes 113, 117 adjacent to the left ventricle.

Unipolar pacing and/or sensing in the left ventricle may be implemented, for example, using the LV distal electrode referenced to the can electrode 209. The LV distal electrode 113 and the LV proximal electrode 117 may be used together as bipolar sense and/or pace electrodes for the left ventricle. The left ventricular lead 106 and the right ventricular lead 104, in conjunction with the ICD 100, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 105 includes a RA-tip electrode 156 and an RA-ring electrode 154 positioned at appropriate locations in the right atrium 120 for sensing and pacing the right atrium 120. In one configuration, the RA-tip 156 referenced to the can electrode 209, for example, may be used to provide unipolar pacing and/or sensing in the right atrium 120. In another configuration, the RA-tip electrode 156 and the RA-ring electrode 154 may be used to effect bipolar pacing and/or sensing.

FIG. 1 illustrates one embodiment of a left atrial lead system 108. In this example, the left atrial lead 108 is implemented as an extracardiac lead with LA distal 118 and LA proximal 115 electrodes positioned at appropriate locations outside the heart 101 for sensing and pacing the left atrium 122. Unipolar pacing and/or sensing of the left atrium may be accomplished, for example, using the LA distal electrode 118 to the can 209 pacing vector. The LA proximal 115 and LA distal 118 electrodes may be used together to implement bipolar pacing and/or sensing of the left atrium 122.

Figure 2A:
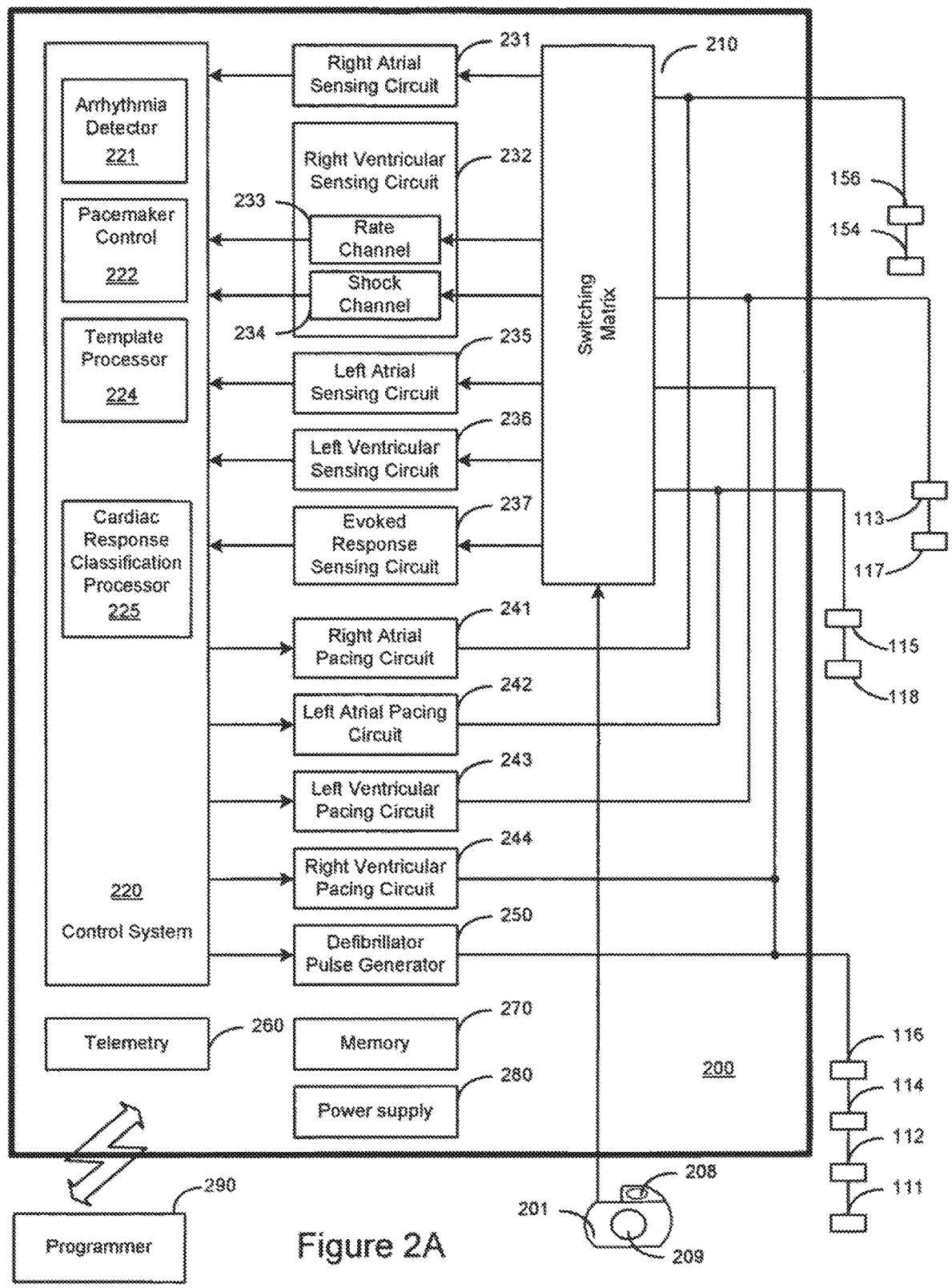
FIG. 2A is a block diagram of an implantable medical device that may be used to classify a cardiac response to pacing in accordance with embodiments of the invention.

Referring now to FIG. 2A, there is shown an embodiment of a cardiac defibrillator 200 suitable for implementing a cardiac response classification methodology of the present invention. FIG. 2A shows a cardiac defibrillator divided into functional blocks. It is understood by those skilled in the art that there exist many possible configurations in which these functional blocks can be arranged. The example depicted in FIG. 2A is one possible functional arrangement. Other arrangements are also possible. For example, more, fewer or different functional blocks may be used to describe a cardiac defibrillator suitable for implementing the cardiac response classification methodology of the present invention. In addition, although the cardiac defibrillator 200 depicted in FIG. 2 contemplates the use of a programmable microprocessor-based logic circuit, other circuit implementations may be utilized.

The cardiac defibrillator 200 depicted in FIG. 2 includes circuitry for receiving cardiac signals from a heart and delivering electrical stimulation energy to the heart in the form of pacing pulses or defibrillation shocks. In one embodiment, the circuitry of the cardiac defibrillator 200 is encased and hermetically sealed in a housing 201 suitable for implanting in a human body. Power to the cardiac defibrillator 200 is supplied by an electrochemical battery 280. A connector block (not shown) is attached to the housing 201 of the cardiac defibrillator 200 to allow for the physical and electrical attachment of the lead system conductors to the circuitry of the cardiac defibrillator 200.

The cardiac defibrillator 200 may be a programmable microprocessor-based system, including a control system 220 and a memory 270. The memory 270 may store parameters for various pacing, defibrillation, and sensing modes, along with other parameters. Further, the memory 270 may store data indicative of cardiac signals received by other components of the cardiac defibrillator 200. The memory 270 may be used, for example, for storing historical EGM and therapy data. The historical data storage may include, for example, data obtained from long term patient monitoring used for trending or other diagnostic purposes. Historical data, as well as other information, may be transmitted to an external programmer unit 290 as needed or desired.

The control system 220 and memory 270 may cooperate with other components of the cardiac defibrillator 200 to control the operations of the cardiac defibrillator 200. The control system depicted in FIG. 2 incorporates a cardiac response classification processor 225 for classifying cardiac responses to pacing stimulation in accordance with various embodiments of the present invention. The control system 220 may include additional functional components including a pacemaker control circuit 222, an arrhythmia detector 221, and a template processor 224 for cardiac signal morphology analysis, along with other components for controlling the operations of the cardiac defibrillator 200.

Telemetry circuitry 260 may be implemented to provide communications between the cardiac defibrillator 200 and an external programmer unit 290. In one embodiment, the telemetry circuitry 260 and the programmer unit 290 communicate using a wire loop antenna and a radio frequency telemetric link, as is known in the art, to receive and transmit signals and data between the programmer unit 290 and the telemetry circuitry 260. In this manner, programming commands and other information may be transferred to the control system 220 of the cardiac defibrillator 200 from the programmer unit 290 during and after implant. In addition, stored cardiac data pertaining to capture threshold, capture detection and/or cardiac response classification, for example, along with other data, may be transferred to the programmer unit 290 from the cardiac defibrillator 200.

In the embodiment of the cardiac defibrillator 200 illustrated in FIG. 2, electrodes RA-tip 156, RA-ring 154, RV-tip 112, RV-ring 111, RV-coil 114, SVC-coil 116, LV distal electrode 113, LV proximal electrode 117, LA distal electrode 118, LA proximal electrode 115, indifferent electrode 208, and can electrode 209 are coupled through a switch matrix 210 to sensing circuits 231-237.

A right atrial sensing circuit 231 serves to detect and amplify electrical signals from the right atrium of the heart. Bipolar sensing in the right atrium may be implemented, for example, by sensing voltages developed between the RA-tip 156 and the RA-ring 154. Unipolar sensing may be implemented, for example, by sensing voltages developed between the RA-tip 156 and the can electrode 209. Outputs from the right atrial sensing circuit are coupled to the control system 220.

A right ventricular sensing circuit 232 serves to detect and amplify electrical signals from the right ventricle of the heart. The right ventricular sensing circuit 232 may include, for example, a right ventricular rate channel 233 and a right ventricular shock channel 234. Right ventricular cardiac signals sensed through use of the RV-tip 112 electrode are right ventricular near-field signals and are denoted RV rate channel signals. A bipolar RV rate channel signal may be sensed as a voltage developed between the RV-tip 112 and the RV-ring 111. Alternatively, bipolar sensing in the right ventricle may be implemented using the RV-tip electrode 112 and the RV-coil 114. Unipolar rate channel sensing in the right ventricle may be implemented, for example, by sensing voltages developed between the RV-tip 112 and the can electrode 209.

Right ventricular cardiac signals sensed through use of the RV-coil electrode 114 are far-field signals, also referred to as RV morphology or RV shock channel signals. More particularly, a right ventricular shock channel signal may be detected as a voltage developed between the RV-coil 114 and the SVC-coil 116. A right ventricular shock channel signal may also be detected as a voltage developed between the RV-coil 114 and the can electrode 209. In another configuration the can electrode 209 and the SVC-coil electrode 116 may be electrically shorted and a RV shock channel signal may be detected as the voltage developed between the RV-coil 114 and the can electrode 209/SVC-coil 116 combination.

Outputs from the right ventricular sensing circuit 232 are coupled to the control system 220. In one embodiment of the invention, rate channel signals and shock channel signals may be used to develop morphology templates for analyzing cardiac signals. In this embodiment, rate channel signals and shock channel signals may be transferred from the right ventricular sensing circuit 232 to the control system 220 and to a template processor 224 where the morphological characteristics of a cardiac signal are analyzed. The template processor 224 works in combination with the control system 220 and the memory 270 to generate and maintain various types of templates, including, for example, templates used for arrhythmia discrimination as well as cardiac response classification as described in more detail below.

Left atrial cardiac signals may be sensed through the use of one or more left atrial electrodes 115, 118, which may be configured as epicardial electrodes. A left atrial sensing circuit 235 serves to detect and amplify electrical signals from the left atrium of the heart. Bipolar sensing and/or pacing in the left atrium may be implemented, for example, using the LA distal electrode 118 and the LA proximal electrode 115. Unipolar sensing and/or pacing of the left atrium may be accomplished, for example, using the LA distal electrode 118 to can vector 209 or the LA proximal electrode 115 to can vector 209.

A left ventricular sensing circuit 236 serves to detect and amplify electrical signals from the left ventricle of the heart. Bipolar sensing in the left ventricle may be implemented, for example, by sensing voltages developed between the LV distal electrode 113 and the LV proximal electrode 117. Unipolar sensing may be implemented, for example, by sensing voltages developed between the LV distal electrode 113 or the LV proximal electrode 117 to the can electrode 209.

Optionally, an LV coil electrode (not shown) may be inserted into the patient's cardiac vasculature, e.g., the coronary sinus, adjacent the left heart. Signals detected using combinations of the LV electrodes, 113, 117, LV coil electrode (not shown), and/or can electrodes 209 may be sensed and amplified by the left ventricular sensing circuitry 236. The output of the left ventricular sensing circuit 236 is coupled to the control system 220.

The outputs of the switching matrix 210 may be operated to couple selected combinations of electrodes 111, 112, 113, 114, 115, 116, 117, 118, 156, 154 to an evoked response sensing circuit 237. The evoked response sensing circuit 237 serves to sense and amplify voltages developed using various combinations of electrodes for cardiac response classification in accordance with embodiments of the invention.

In the embodiments described below, various combinations of pacing and sensing electrodes may be utilized in connection with pacing and sensing the cardiac signal following the pace pulse to classify the cardiac response to the pacing pulse. For example, in some embodiments, a first electrode combination is used for pacing a heart chamber and a second electrode combination is used to sense the cardiac signal following pacing. In other embodiments, the same electrode combination is used for pacing and sensing.

Sensing the cardiac signal following a pacing pulse using the same electrode combination for both pacing and sensing may yield a sensed cardiac signal including a pacing artifact component associated with residual post pace polarization at the electrode-tissue interface. The pacing artifact component may be superimposed on a smaller signal indicative of the cardiac response to the pacing pulse, i.e., the evoked response. The pacing output circuitry may include a coupling capacitor to block DC components from the heart and to condition the pacing stimulus pulse. A relatively large coupling capacitor may cause a larger pacing artifact that decays exponentially over a relatively large period of time.

The presence of a large pacing artifact signal may complicate the classification of the cardiac response to pacing. Various embodiments of the invention are directed to methods involving detection of a cardiac signal following pacing and canceling the pacing artifact from the detected signal. Classification of the cardiac response to pacing may be implemented using the pacing artifact cancelled signal. Cancellation of the pacing artifact in cardiac response classification is particularly important when the same or similar electrode combinations are used both for delivering pacing pulses and for sensing the cardiac signals following the delivery of the pacing pulses. Cancellation of the pacing artifact may also be used when a first electrode combination is used for pacing the heart chamber and a different electrode combination is used to sense the subsequent cardiac response. Methods and systems for pacing artifact cancellation are described in commonly owned U.S. patent application, Ser. No. 10/335,534, filed Dec. 31, 2002, which is incorporated by reference herein in its entirety.

In various embodiments described herein a first electrode combination may be used for pacing the heart chamber and a second electrode combination used for sensing the cardiac signals following the pace for cardiac response classification. If different electrode combinations are used for pacing and sensing, a temporal separation between the cardiac response signal, e.g., the evoked response, and the pacing artifact may facilitate classification of the cardiac response to pacing. The temporal separation occurs due to the propagation delay of the depolarization wavefront initiated at the pacing electrode and traveling to a sensing electrode that is physically spaced apart from the pacing electrode. The temporal separation of the cardiac response signal and the pacing artifact may be sufficient to obviate cancellation of the pacing artifact. Use of different electrodes for pacing and sensing in connection with capture verification is described in commonly owned U.S. Pat. No. 6,128,535 which is incorporated herein by reference.

The pacemaker control circuit 222, in combination with pacing circuitry for the left atrium, right atrium, left ventricle, and right ventricle 241, 242, 243, 244, may be implemented to selectively generate and deliver pacing pulses to the heart using various electrode combinations. The pacing electrode combinations may be used to effect bipolar or unipolar pacing of the heart chambers as described above As described above, bipolar or unipolar pacing pulses may be delivered to a heart chamber using one of the pacing vectors as described above. The electrical signal following the delivery of the pacing pulses may be sensed through various sensing vectors coupled through the switch matrix 210 to the evoked response sensing circuit 237 and used to classify the cardiac response to pacing.

In one example, the cardiac signal following the pacing pulse may be sensed using the same vector as was used for delivery of the pacing pulse. In this scenario, the pacing artifact may be canceled from the sensed cardiac signal using the pacing artifact cancellation techniques described below. Following cancellation of the pacing artifact, retriggerable classification windows may be defined following the pacing pulse and used to classify the cardiac response to pacing. The cardiac response may be classified as one of a captured response, a non-captured response, a non-captured response and an intrinsic beat, and a fusion/pseudofusion beat, for example.

In another example, the vector used to sense the cardiac signal following the pacing pulse may be different from the vector that was used to deliver the pacing pulse. The sensing vector may be selected to minimize the pacing artifact. Cancellation of the pacing artifact may not be necessary if the pacing artifact is sufficiently minimized using this technique.

In various embodiments, the pacing vector may be a near-field vector and the sensing vector may be a far-field vector. In an example of right ventricular pacing and cardiac response sensing, the pacing vector may be the rate channel vector and the sensing vector may be the shock channel vector. Cardiac response classification may be accomplished, for example, using retriggerable classification windows defined following delivery of the pacing pulse as described in greater detail below.

Possible sensing vectors for effecting cardiac response classification may include, for example, RV-tip 112 and RV-coil 114, RV-coil 114 and LV distal electrode 113, RV coil 114 and LV proximal electrode 117, RV-coil 114 and can 209, RV-coil 114 and SVC coil 116, RV-coil 114 and SVC coil 116 tied and the can 209, RV-coil 114 and A-ring 154, RV-coil 114 and A-tip 156, LV distal electrode 113 and LV proximal electrode 117, LV distal electrode 113 and can 209, LV distal electrode 113 and SVC coil 116, LV distal electrode 113 and A-ring 154, LV distal electrode 113 and A-tip 156, LV proximal electrode 117 and can 209, LV proximal electrode 117 and SVC coil 116, LV proximal electrode 117 and. A-ring 154, LV proximal electrode 117 and RA-tip 156, SVC coil 116 and can 209, RA-ring 154 and can 209, RA-tip 156 and can 209, SVC coil 116 and A-ring 154, SVC coil 116 and A-tip 156, RA-ring 154 and RA-tip 156, RA-ring 154 and can 209, RA-tip 156 and RV-coil 114, RA-ring 154 and RV-coil 114, RA-tip 156 and RV-tip 112, RA-ring 154 and RV-tip 112, RV-tip 112 and can 209, RV-ring 111 and can 209, LV distal electrode 113 and RV-coil 114, LV proximal electrode 117 and RV-coil 114, LV distal electrode 113 and RV-ring 111, and LV distal electrode 113 and RV-ring 111. This list is not exhaustive and other sensing vector combinations may be developed to implement cardiac response classification in accordance with embodiments of the invention. For example, other combinations may include a coronary sinus electrode, an indifferent electrode, a leadless ECG electrode, cardiac epicardial electrodes, subcutaneous electrodes, and/or other electrodes.

Approaches for using leadless ECG electrodes for capture detection are described in U.S. Pat. No. 5,222,493, which is incorporated by reference in its entirety.

Subcutaneous electrodes may provide additional sensing vectors useable for cardiac response classification. In one implementation, cardiac rhythm management system may involve a hybrid system including an intracardiac device configured to pace the heart and an extracardiac device, e.g., a subcutaneous defibrillator, configured to perform functions other than pacing. The extracardiac device may be employed to detect and classify cardiac response to pacing based on signals sensed using subcutaneous electrode arrays. The extracardiac and intracardiac devices may operate cooperatively with communication between the devices occurring over a wireless link, for example. Examples of subcutaneous electrode systems and devices are described in commonly owned U.S. patent applications Ser. No. 10/462,001, filed Jun. 13, 2003 and Ser. No. 10/465,520, filed Jun. 19, 2003, which are incorporated herein by reference in their respective entireties.

For right ventricular pacing, bipolar pacing may be delivered using the RV-tip electrode 112 and the RV-ring electrode 111. Unipolar pacing may be delivered using the RV-tip 112 to can 209 vector. The preferred sensing electrode combinations for cardiac response classification following RV pacing include RV-coil 114 to SVC-coil 116 tied to the can electrode 209, RV-coil 114 to can electrode 209, and, if the system includes a left ventricular lead, LV distal electrode 113 to LV proximal electrode 117.

In an example of left ventricular pacing, bipolar pacing pulses may be delivered to the left ventricle between the LV distal electrode 113 and the LV proximal electrode 117. In another example, unipolar pacing pulses may be delivered to the left ventricle, for example, between the LV distal electrode 113 and the can 209. The cardiac signal following the delivery of the pacing pulses may preferably be sensed using the LV proximal electrode 117 and the can 209.

In an example of right atrial pacing, bipolar pacing pulses may be delivered to the right atrium between the RA-tip electrode 156 and the RA-ring electrode 154. In another example, unipolar pacing pulses may be delivered to the right atrium, for example, between the RA-tip electrode 156 and the can electrode 209. For unipolar right atrial pacing, the preferred electrode combination for sensing cardiac signals following pacing for cardiac response classification comprises the RA-ring 154 to indifferent electrode.

In an example of left atrial pacing, bipolar pacing pulses may be delivered to the left atrium between the LA distal electrode 118 and the LA proximal electrode 115. In another example, unipolar pacing pulses may be delivered to the left atrium, for example, between the LA distal electrode 118 and the can electrode 209. The cardiac signal following the delivery of the pacing pulses and used for cardiac response classification may preferably be sensed using the RA-tip 156 to RA-ring 154 vector.

In one embodiment of the invention, a switching matrix 210 is coupled to the RA-tip 156, RA-ring 154, RV-tip 112, RV-coil 114, LV distal electrode 113, LV proximal electrode 117, SVC coil 116, LA distal electrode 118, LA proximal electrode 115, indifferent, and can 209 electrodes. The switching matrix 210 may be arranged to provide connections to various configurations of pacing and defibrillation electrodes. The outputs of the switching matrix 210 are coupled to an evoked response (ER) sensing circuit 237 that serves to sense and amplify cardiac signals detected between the selected combinations of electrodes. The detected signals are coupled through the ER amplifier 237 to a cardiac response classification processor 225. The cardiac response classification processor 225 includes circuitry configured to classify a cardiac response to a pacing stimulation, including, for example, classifying a captured response, a non-captured response, an intrinsic beat added to a non-captured response, and a fusion/pseudofusion response, in accordance with the invention.

Figure 2B:
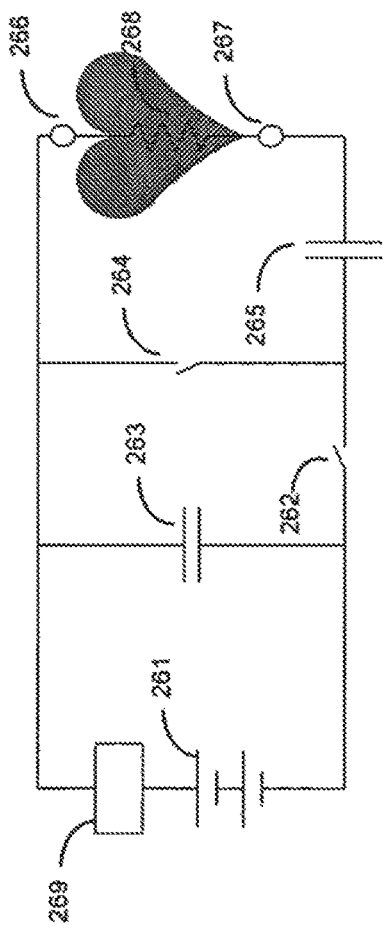
FIG. 2B is a schematic diagram of a circuit that may be used to generate pacing stimulations in accordance with embodiments of the invention.
Figure 2C:
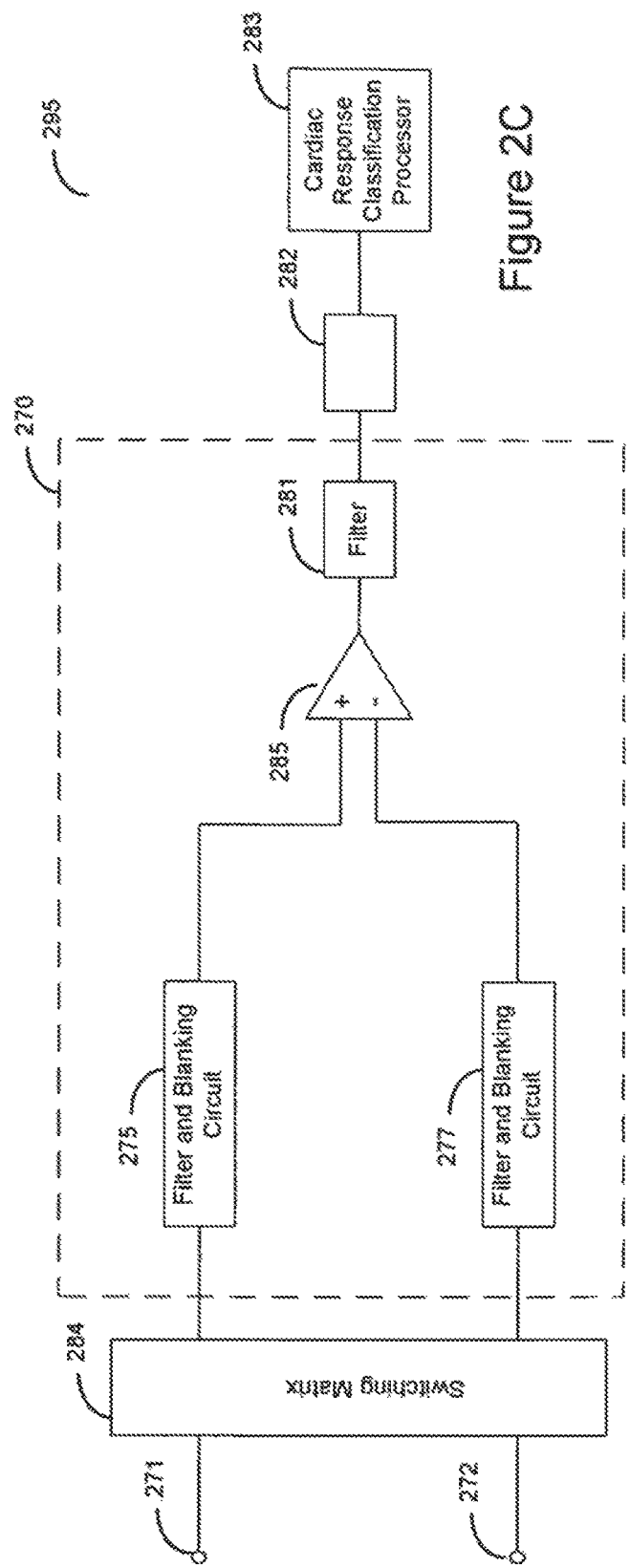
FIG. 2C is a schematic diagram of a circuit that may be used to sense a cardiac signal following the delivery of a pacing stimulation and to classify the cardiac response to the pacing stimulation according to embodiments of the invention.

FIGS. 2B and 2C illustrate more detailed examples of pacing and sensing circuitry, respectively, that may be used for cardiac pace/sense channels of a pacemaker in accordance with embodiments of the invention. It will be appreciated that the example pacing and sensing circuits illustrated in FIGS. 2B and 2C may be arranged to achieve the pacing and sensing vectors described above.

In example embodiments of the invention, the pacing circuit of FIG. 2B includes a power supply or battery 261, a first switch 262, a second switch 264, a pacing charge storage capacitor 263, coupling capacitor 265, and a pacer capacitor charging circuit 269 all of which are cooperatively operable under the direction of a controller of known suitable construction. The power supply or battery 261 is preferably the battery provided to power the pacemaker and may comprise any number of commercially available batteries suitable for pacing applications. The switches 262, 264 may be implemented using any number of conventionally available switches. The pacing capacitor charging circuit 269 includes circuitry to regulate the voltage across the pacing charge storage capacitor 263.

The pacing charge storage capacitor 263 may also comprise any number of conventional storage capacitors that can be used to develop a sufficient pacing charge for stimulating the heart. The primary function of the coupling capacitor 265 is to attenuate the polarization voltage or "afterpotential" which results from pacing and additionally block any DC signals from reaching the heart 268 during pacing. The coupling capacitor 265 may have a capacitance, for example, in the range of about 2 microfarads to about 22 microfarads. Energy stored in the pacing charge storage capacitor 263 may be delivered to the heart 268 using various combinations of cardiac electrodes 266, 267, as described above.

FIG. 2C illustrates a block diagram of circuit 295 that may be used to sense cardiac signals following the delivery of a pacing stimulation and classify the cardiac response to the pacing stimulation according to embodiments of the invention. A switch matrix 284 is used to couple the cardiac electrodes 271, 272 in various combinations discussed above to the sensing portion 270 of the cardiac response classification circuit 295. The sensing portion 270 includes filtering and blanking circuitry 275, 277, sense amplifier 285, band pass filter 281, and window generation and signal characteristic detector 282. The window generation and signal characteristic detector 282 is coupled to a cardiac response classification processor 283.

A control system, e.g., the control system 220 depicted in FIG. 2A, is operatively coupled to components of the cardiac response classification circuit 295 and controls the operation of the cardiac response classification circuit 295, including the filtering and blanking circuits 275, 277. Following a blanking period of sufficient duration following delivery of the pacing stimulation, the blanking circuitry 275, 277 operates to allow detection of a cardiac signal responsive to the pacing stimulation. The cardiac signal is filtered, amplified, and converted from analog to digital form. The digitized signal is communicated to the cardiac response classification processor 283 which operates in cooperation with other components of the control system 220, FIG. 2A to classify cardiac responses to pacing according to embodiments of the invention.

Figure 3:
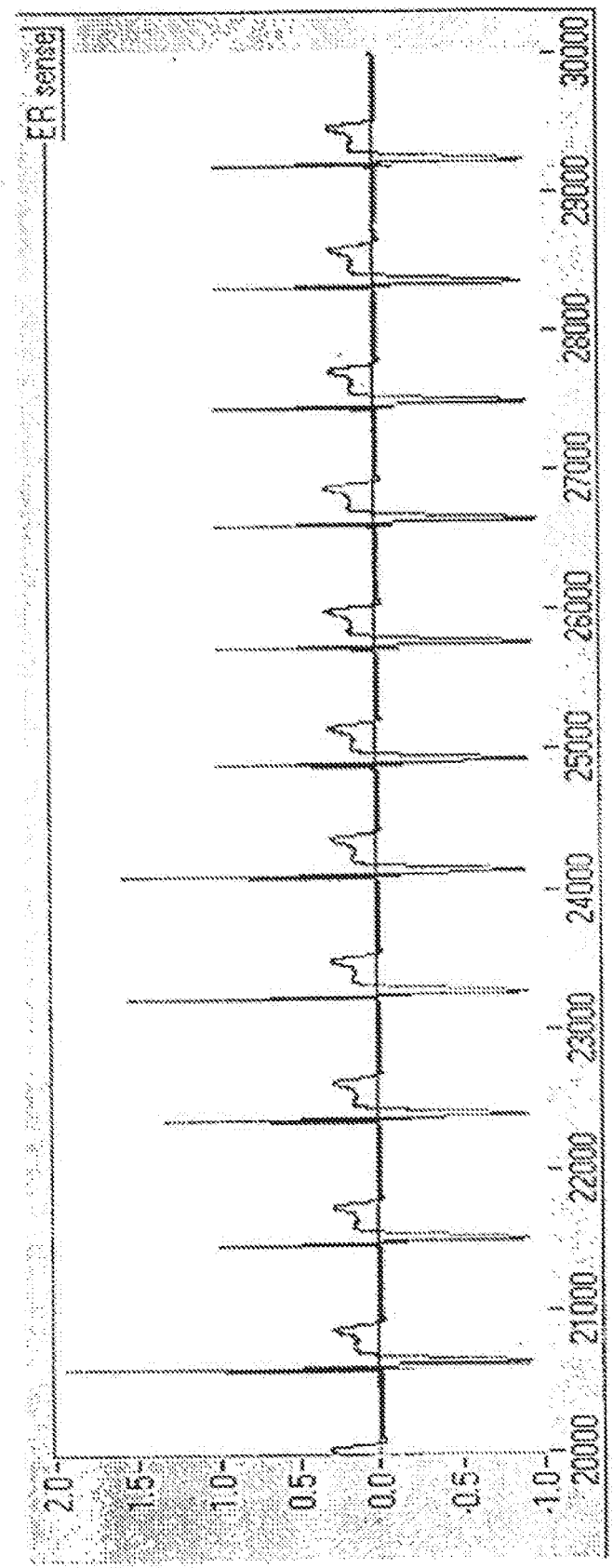
FIG. 3 is a graph of a cardiac signal that indicates consistent capture.

When pacing pulses delivered to the heart produce a depolarization wave in cardiac tissue resulting in a cardiac contraction, a captured response may be detected by examining the cardiac signal following the delivery of the pacing pulse. FIG. 3 is a graph illustrating the output of the sensing portion 270 of the cardiac response classification circuit 295 of FIG. 2C in which the cardiac signal consistently indicates capture following a sequence of pacing pulses. In this example, a pacing pulse is delivered to the heart using the RV-tip and RV-coil electrodes, also referred to herein as a right ventricular rate channel. The cardiac signal following a right ventricular pace is sensed using a RV-coil to SVC-coil+can sensing vector, also referred to herein as the shock channel.

Figure 4A:
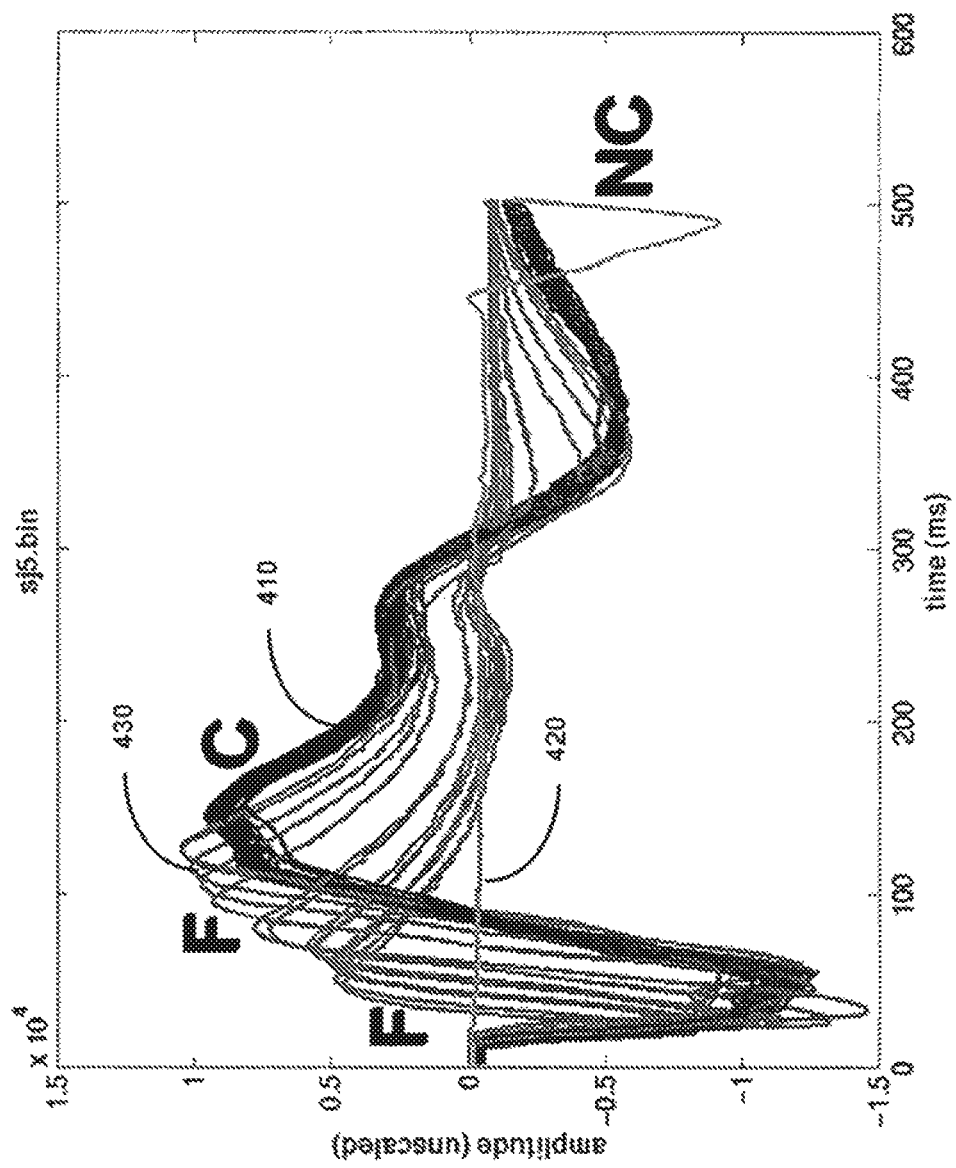
FIG. 4A depicts superimposed graphs of captured responses, non-captured responses, and fusion/pseudofusion beats in accordance with embodiments of the invention.
Figure 4B:
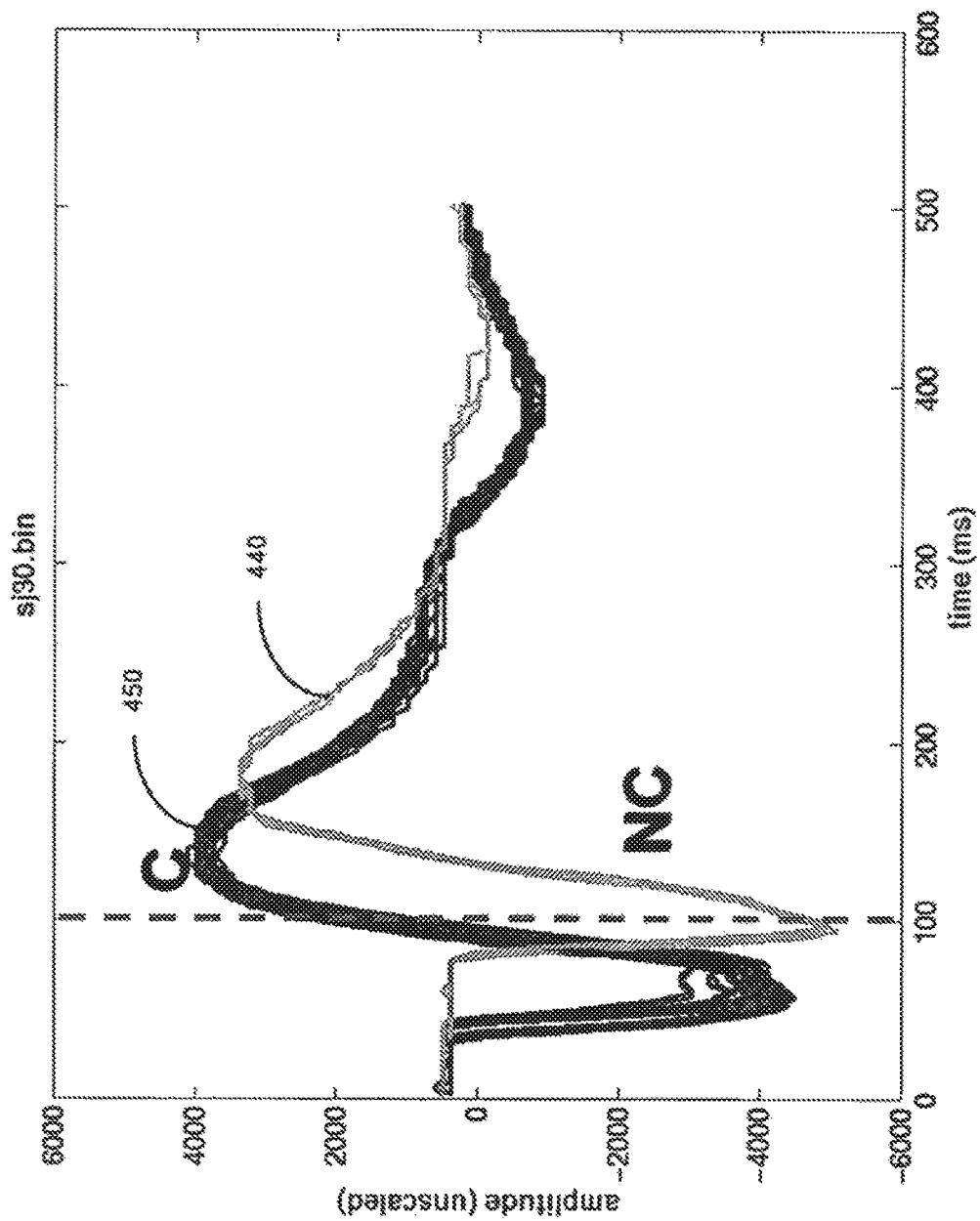
FIG. 4B depicts superimposed graphs comparing an early intrinsic beat and a captured response in accordance with embodiments of the invention.

FIG. 4A depicts superimposed graphs of captured responses 410, non-captured responses 420, and fusion/pseudofusion beats 430. FIG. 4B depicts superimposed graphs comparing an early intrinsic beat 440 and a captured response 450. The graphs of FIGS. 4A and 4B represent the cardiac signal following the pacing stimulation if the pacing pulse is delivered on the RV rate channel and the cardiac signal following pacing is sensed on the RV shock channel. The captured response exhibits a consistent morphology when detected on this vector, as illustrated in the graphs of FIGS. 4A and 4B.

Figure 4C:
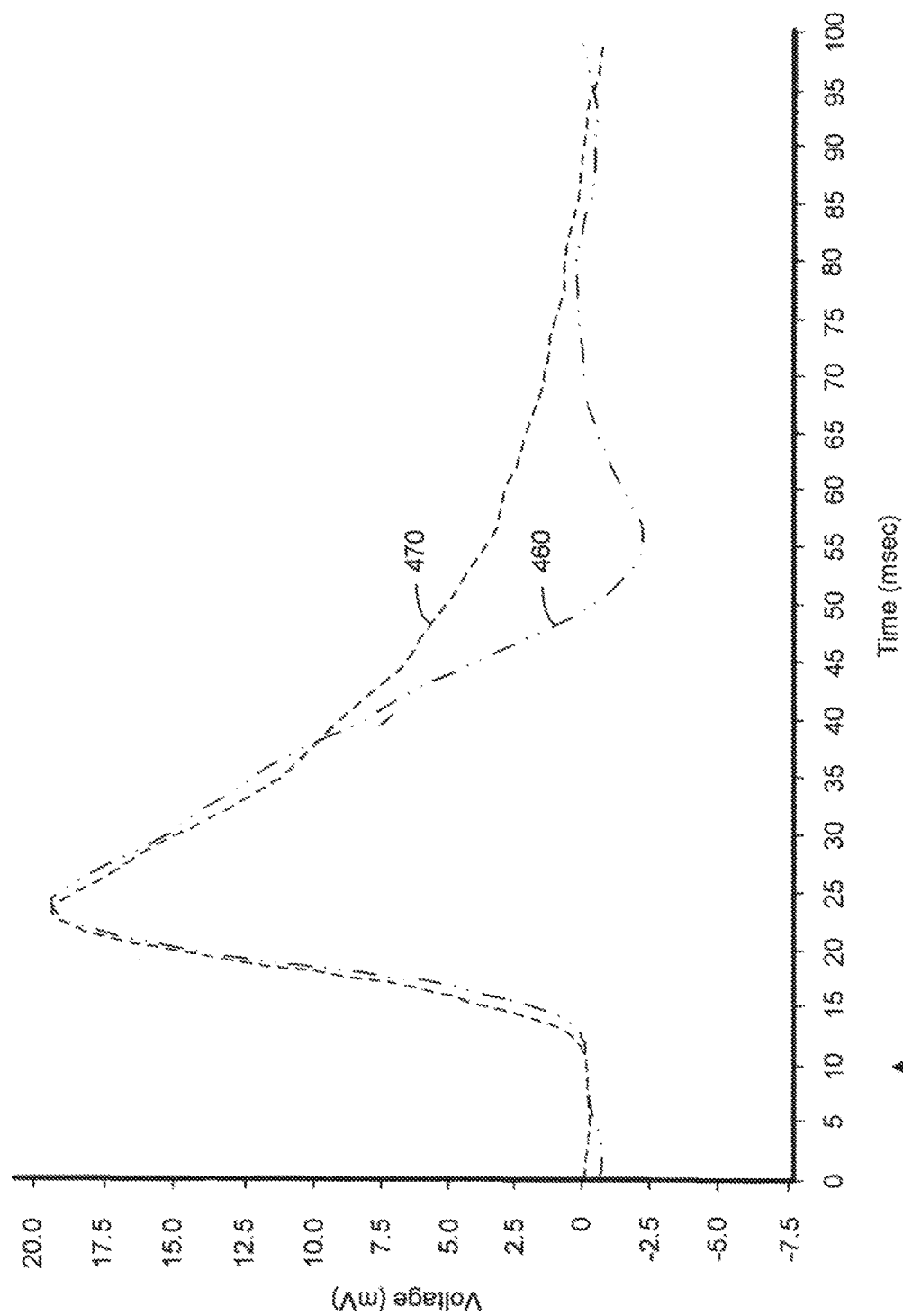
FIG. 4C illustrates superimposed graphs of a captured response and a non-captured response in accordance with embodiments of the invention.

In another example, the same vector may be used to pace the heart chamber and sense the cardiac signal following the pace to classify the cardiac response. Pacing in the right ventricle may be accomplished using the pacing vector RV-tip to RV-ring, for example. FIG. 4C illustrates superimposed graphs of a captured response 460 and a non-captured response 470 sensed using the same sensing vector, e.g., RA-tip to RA-ring.

Figure 5:
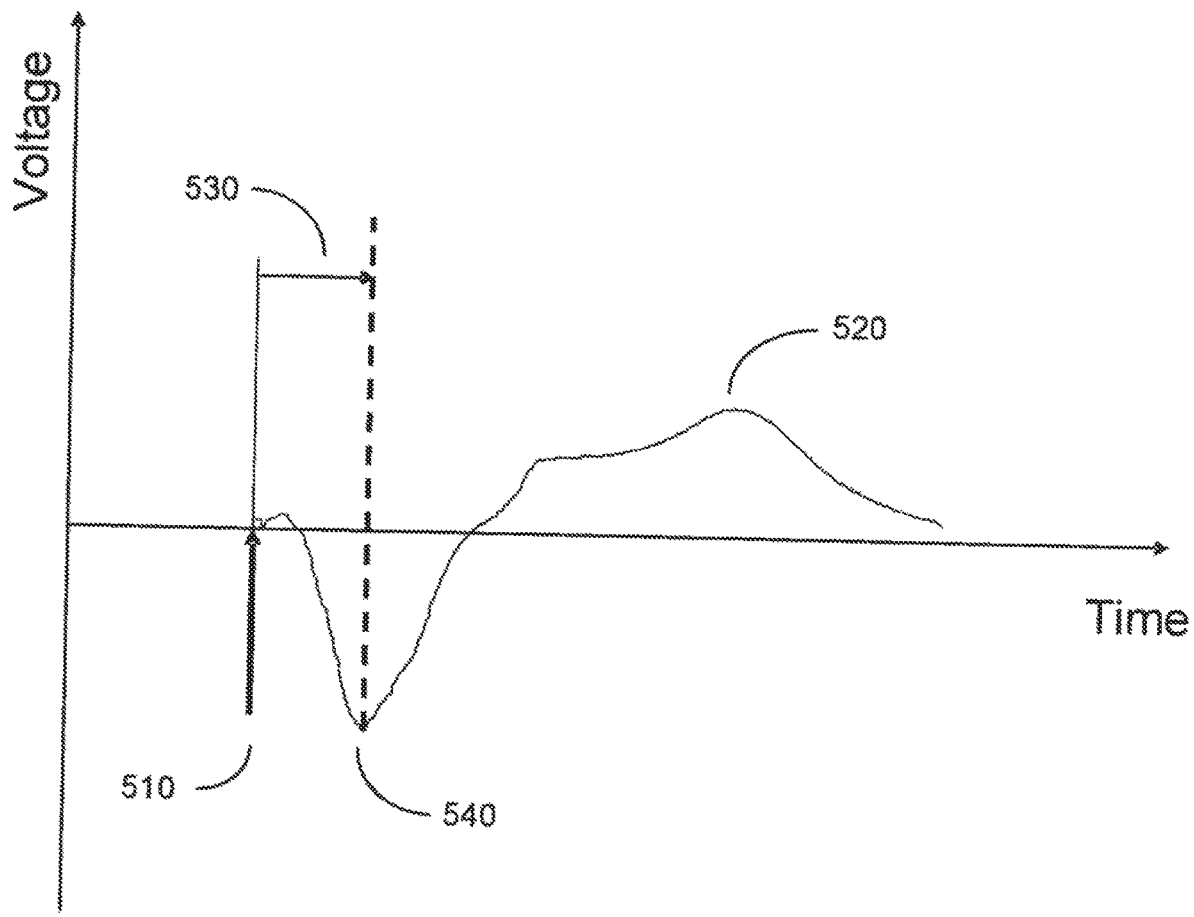
FIG. 5 is a graph illustrating a cardiac signal sensed on a right ventricular (RV) shock channel vector following a pacing pulse delivered on a rate channel in accordance with embodiments of the invention.

As previously discussed, if a first vector, e.g., rate channel vector RV-tip to RV-coil, is used to deliver a pacing pulse and a second vector, e.g., shock channel vector RV-coil to SVC-coil or RV-coil to SVC-coil+can, is used to sense the cardiac signal responsive to the pacing pulse, the pacing artifact is separated from the evoked response due to a propagation delay from RV-tip to RV-coil. FIG. 5 is a graph illustrating a cardiac signal 520 sensed on a right ventricular (RV) shock channel vector following a pacing pulse 510 delivered on a rate channel. The cardiac signal 520 exhibits a propagation delay 530, for example, a propagation delay of about 55 ms, between the pacing pulse 510 and the portion of the cardiac signal indicating a captured response 540.

Figure 6:
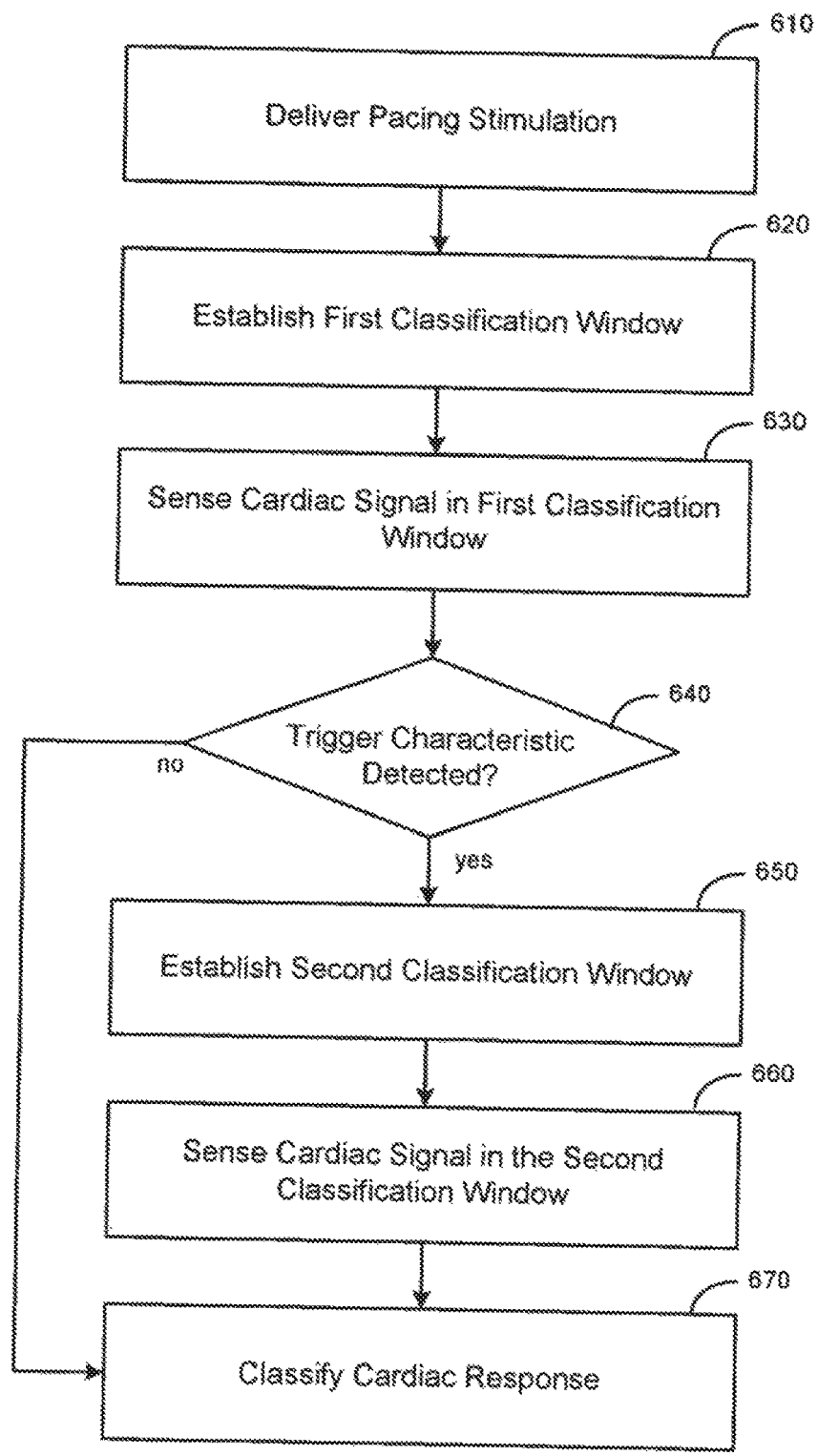
FIG. 6 is a flowchart illustrating a method of classifying a cardiac response to pacing using retriggerable classification windows in accordance with embodiments of the invention.

FIG. 6 is a flowchart illustrating a method of classifying a cardiac response to a pacing stimulation in accordance with embodiments of the invention. In this method the same electrode combination may be used for pacing and sensing, or a first electrode combination may be used for pacing and a second electrode combination may be used for sensing. If the same electrode combination is used for pacing and sensing, then pacing artifact cancellation may facilitate cardiac response classification. In accordance with this method, a pacing stimulation is delivered 610 to a heart and a first cardiac response classification window is established 620 subsequent to delivery of the pacing stimulation.

The pacing stimulation may be delivered to any heart chamber. For example, the pacing stimulation may be delivered to the right ventricle, the left ventricle, the right atrium, and the left atrium.

The cardiac signal is sensed 630 in the first cardiac response classification window. If a trigger feature of the cardiac signal is detected 640 in the first classification window, a second cardiac response classification window is established 650. The cardiac signal is sensed 660 in the second cardiac response classification window. The cardiac response to the pacing stimulation delivered to the chamber or combination of chambers is classified 670 based on one or more characteristics of the cardiac signal. Although in various examples provided herein, the cardiac response classification windows are represented as contiguous and non-overlapping, the classification windows may be overlapping and/or may involve a delay interval defined between classification windows.

Figure 7:
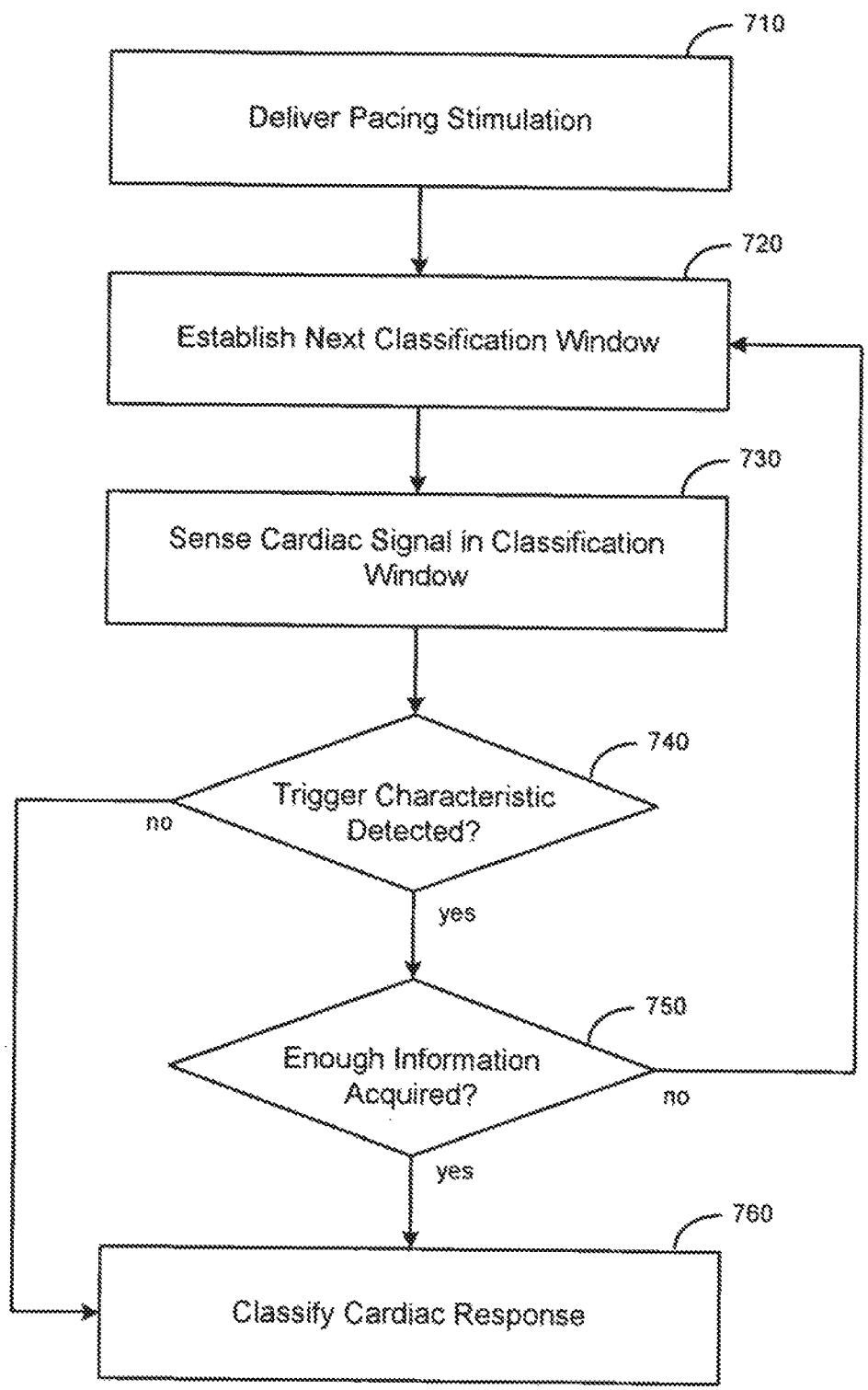
FIG. 7 is a flowchart illustrating a method of triggering multiple cardiac response classification windows in accordance with embodiments of the invention.

The process of establishing cardiac response classification windows if trigger characteristics are detected in previous cardiac response classification windows may continue until a sufficient amount of information is acquired for classifying the cardiac response. The flowchart of FIG. 7 illustrates a method of triggering multiple cardiac response classification windows in accordance with embodiments of the invention. A pacing stimulation is delivered to the heart 710 and a cardiac response classification window is established 720 subsequent to the delivery of the pacing stimulation. A cardiac signal following the pacing stimulation is sensed in the classification window. If a trigger characteristic is detected 740, more information is needed 750 to classify the cardiac response. The next classification window is established 720. Additional classification windows are established to facilitate the acquisition of additional cardiac signal information as indicated in process blocks 720-740. If enough information is acquired, then the cardiac response is classified 760.

In the example process illustrated in FIG. 7, the trigger characteristic may comprise the absence of sufficient information to classify the cardiac response. This situation may arise, for example, if a cardiac signal feature indicative of a particular cardiac response type is not detected, but additional information is desired before eliminating the particular cardiac response type as the cardiac response. Further, this situation may arise if a cardiac signal feature indicative of a particular cardiac response type is detected, but additional information is required to classify the cardiac response. Additional information may also be required to classify the cardiac response if the cardiac signal is detected as noisy.

Figure 8:
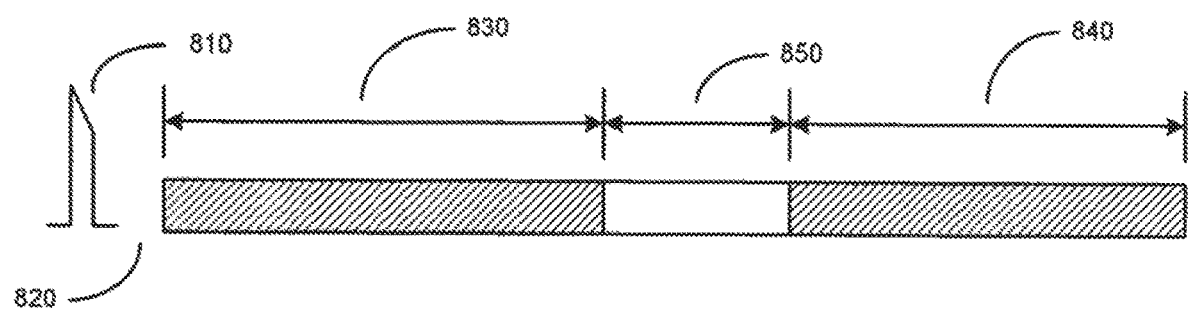
FIG. 8 is a diagram illustrating a retriggerable cardiac response classification window in accordance with embodiments of the invention.

FIG. 8 is a diagram illustrating a retriggerable cardiac response classification window in accordance with embodiments of the invention. A pacing stimulation 810 is delivered to the heart, for example, to the right ventricle. The cardiac signal is blanked for a period of time 820, for example, about 0 ms to about 40 ms, following the delivery of the pacing stimulation 810. After the blanking period 820, a first cardiac response classification window 830 is established. The length of the first cardiac response classification window may be a programmable length, for example, less than about 325 ms. The cardiac signal following the pacing pulse is sensed during the first cardiac response classification window 830. If a trigger characteristic is detected within the first cardiac response classification window, then a second cardiac response classification window 840 is triggered. The length of the second cardiac response classification window may be programmable, and may have a length less than about 325 ms. The length of the second classification window may be different from the length of the first classification window. Alternatively, the lengths of the first and the second classification windows may be the same.

A delay period 850 may be established between the end of the first cardiac response classification window 830 and the beginning of the second cardiac response classification window 840. The length of the delay may be in a range of about 0 ms (no delay) to about 40 ms, for example. The cardiac signal is sensed in the second cardiac response classification window 840 if the second cardiac response classification window 840 is triggered. The cardiac response to the pacing stimulation 810 is classified based on characteristics of the sensed cardiac signal.

Figure 9:
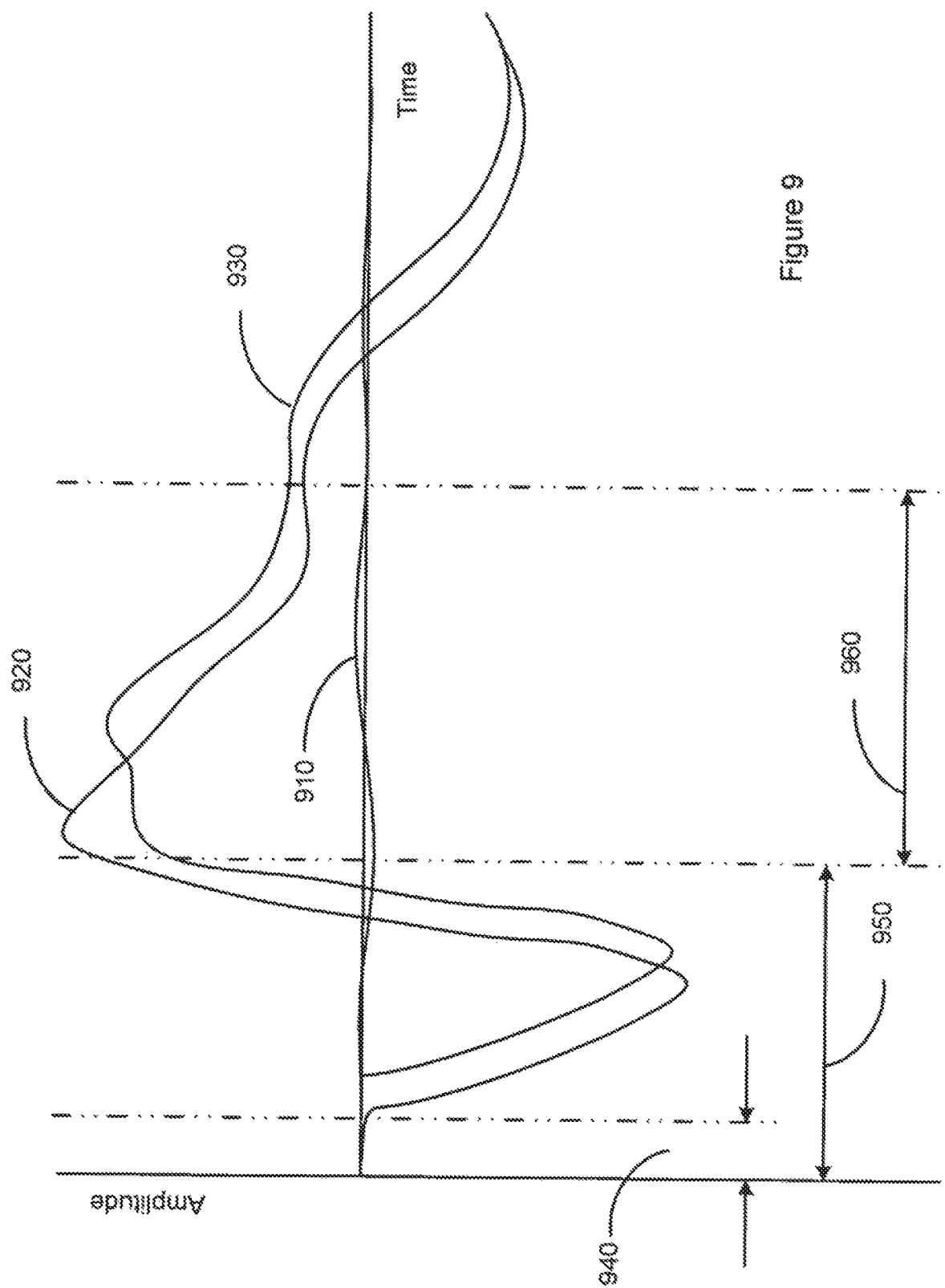
FIG. 9 illustrates cardiac signals indicative of a variety of cardiac pacing responses and their relation to the cardiac response classification windows in accordance with embodiments of the invention.

FIG. 9 illustrates cardiac signals indicative of a variety of cardiac pacing responses and their relation to the cardiac response classification windows in accordance with embodiments of the invention. In the depiction of FIG. 9, cardiac signals indicative of a non-captured response 910, a captured response 930 and a fusion/pseudofusion beat 920 are illustrated. A blanking period 940 follows delivery of the pacing pulse. A first classification window 950 begins after the pacing pulse. If a trigger characteristic of the cardiac signal is detected in the first classification window, a second classification window 960 is established.

Figure 10:
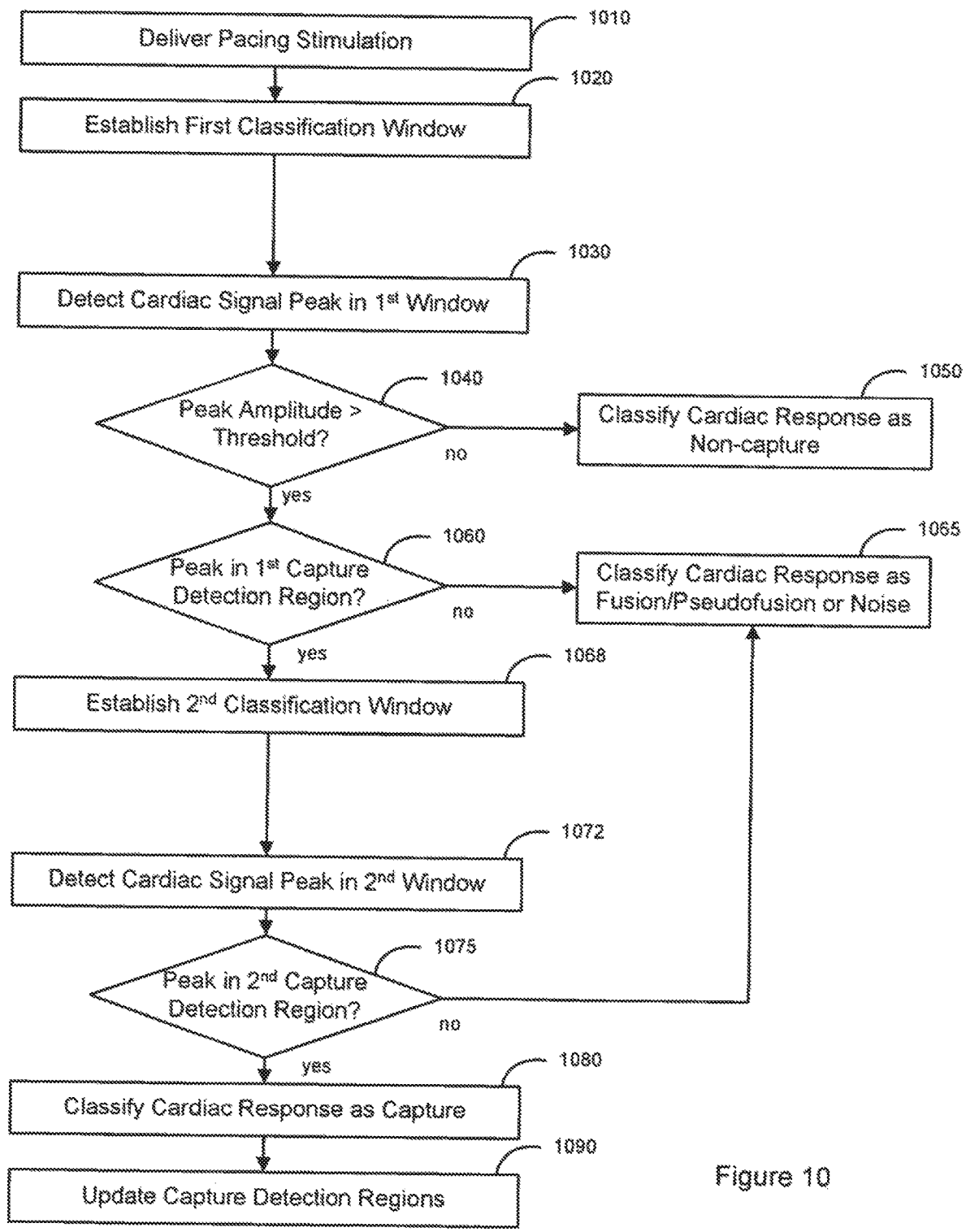
FIG. 10 is a flowchart illustrating a method of classifying a cardiac response to pacing using capture detection regions defined in accordance with embodiments of the invention.

The flowchart of FIG. 10 illustrates a method of classifying the cardiac response to pacing in accordance with embodiments of the invention. The process illustrated in FIG. 10 involves first and second capture detection regions respectively defined in the first and the second cardiac response classification windows. The first and second capture detection regions may be defined as functions of time and amplitude. The capture detection regions may be any shape, including, for example, a circle, square, rectangle, or other shape. The first capture detection region may have a shape that is different from the second capture detection region. In this example, a cardiac signal peak detected in the first capture detection region comprises a trigger characteristic for the first cardiac response classification window. The peak of the cardiac signal within a cardiac response classification window may comprise, for example, a signal maximum or signal minimum detected within the cardiac response classification window.

Turning now to FIG. 10, subsequent to the delivery 1010 of a pacing stimulation, a first classification window is established 1020. The cardiac signal is sensed following the pacing stimulation and a peak of the cardiac signal is determined 1030 in the first classification window. If the absolute value of the peak amplitude is less or equal to 1040 a threshold value, then the cardiac response is classified 1050 as a non-captured response. If the absolute value of the peak amplitude is beyond 1040 the threshold value and is detected 1060 in the first capture detection region, then a second classification window is established 1068. In this example, detection 1060 of a peak of the cardiac signal within the first capture detection region comprises a trigger characteristic of the cardiac signal. If the trigger characteristic is detected 1060, then the second classification window is established 1068.

If the peak of the cardiac signal exceeds 1040 the threshold value, but is not detected 1060 in the first capture detection region, then the cardiac response may be classified 1065 as fusion/pseudofusion.

If the second cardiac response classification window is established 1068, the cardiac signal is sensed in the second cardiac response classification window. A peak of the cardiac signal is detected 1072 in the second classification window. If the peak is not detected 1075 in the second capture detection region, then the cardiac response may be classified 1065 as a fusion/pseudofusion. If the peak is detected 1075 in the second capture detection region, then the cardiac response is classified 1080 as a captured response.

The first and/or the second capture detection windows may be updated 1090 based on the characteristics of the sensed cardiac signal. In one implementation, the location of the cardiac signal peaks in the first and the second capture detection windows are combined with previously acquired cardiac signal peaks, for example, by averaging. The new average peak locations may be used to define the locations of subsequent capture detection regions. Various methods and systems for initializing and updating target regions including capture detection regions are described in commonly owned U.S. Patent Application identified by Ser. No. 10/448,260, filed May 28, 2003, which is incorporated herein by reference in its entirety.

Figure 11:
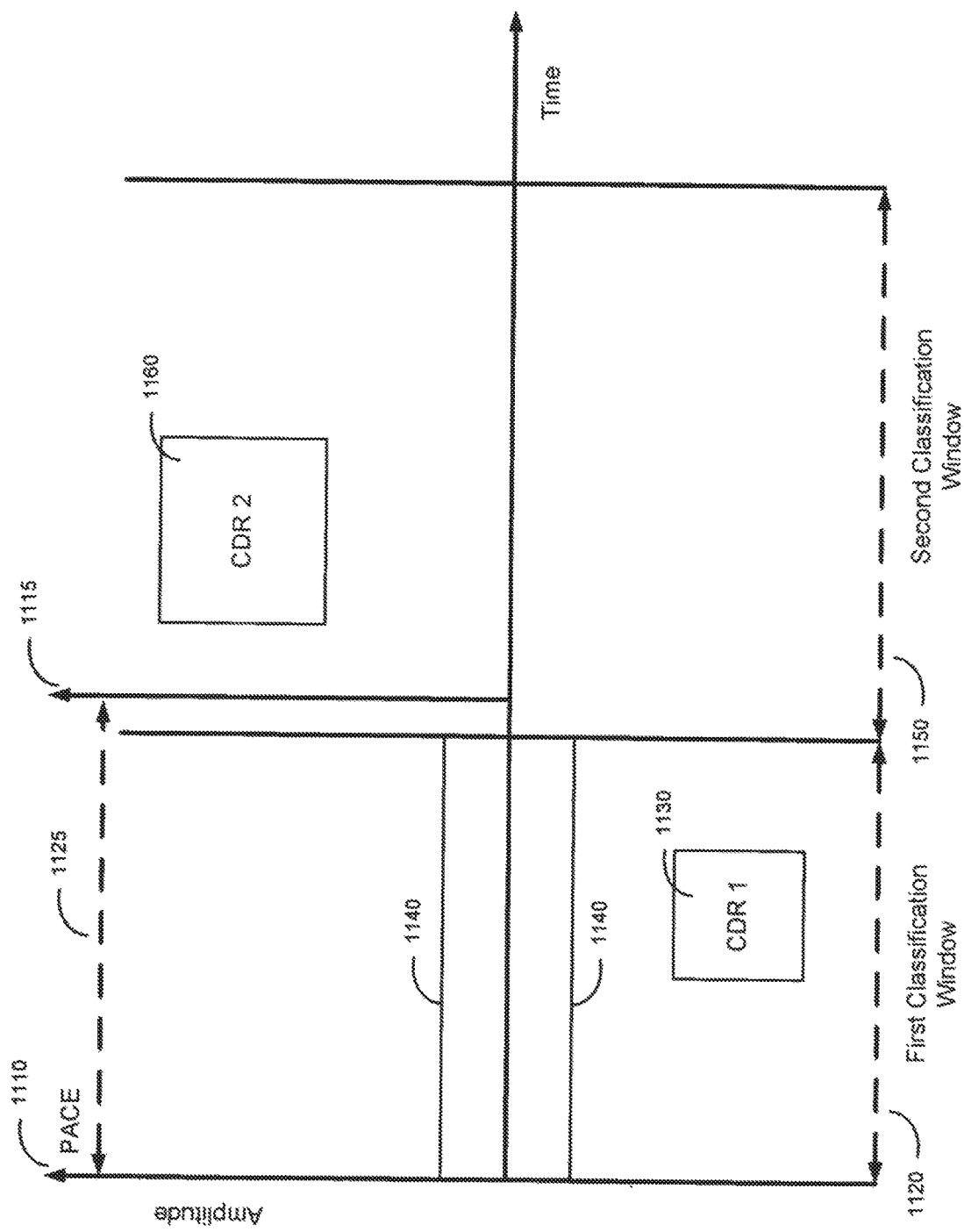
FIG. 11 is a diagram illustrating cardiac response classification windows and capture detection regions in accordance with embodiments of the invention.

FIG. 11 is a diagram illustrating the cardiac response classification windows and the capture detection regions described in connection with FIG. 10 and used in the classifying the cardiac response to pacing in accordance with embodiments of the invention. A pacing stimulation 1110 is delivered to the heart and a first cardiac response classification window 1120 is established subsequent to the delivery of the pacing stimulation 1110. A first capture detection region (CDR) 1130 is defined within the first cardiac response classification window. The cardiac signal following the pacing stimulation is sensed and the peak amplitude is detected. If the peak is less than or equal to a threshold 1140, then the cardiac response is classified as a non-captured response. If the cardiac response is classified as a non-captured response, then a back up pace 1115 may be delivered upon expiration of a back up pace interval 1125. The back up pace interval 1125 may comprise an interval of about 100 ms, for example. If a back up pace is delivered, one or more additional cardiac response classification windows may be established to assess the effectiveness of the back up pace.

If the cardiac signal peak falls within the first capture detection region 1130, then a second cardiac response classification window is established 1150. The cardiac signal is sensed in the second cardiac response classification window and a peak of the cardiac signal is detected. If the peak of the cardiac signal falls within the second capture detection region 1160, then the cardiac response is classified as a captured response. The cardiac response may be classified as fusion/pseudofusion if the peak of the cardiac signal falls beyond the boundary of the first capture detection region 1130 in the first classification window 1120 and/or beyond the boundary of the second capture detection region 1160 in the second classification window 1150.

Figure 12:
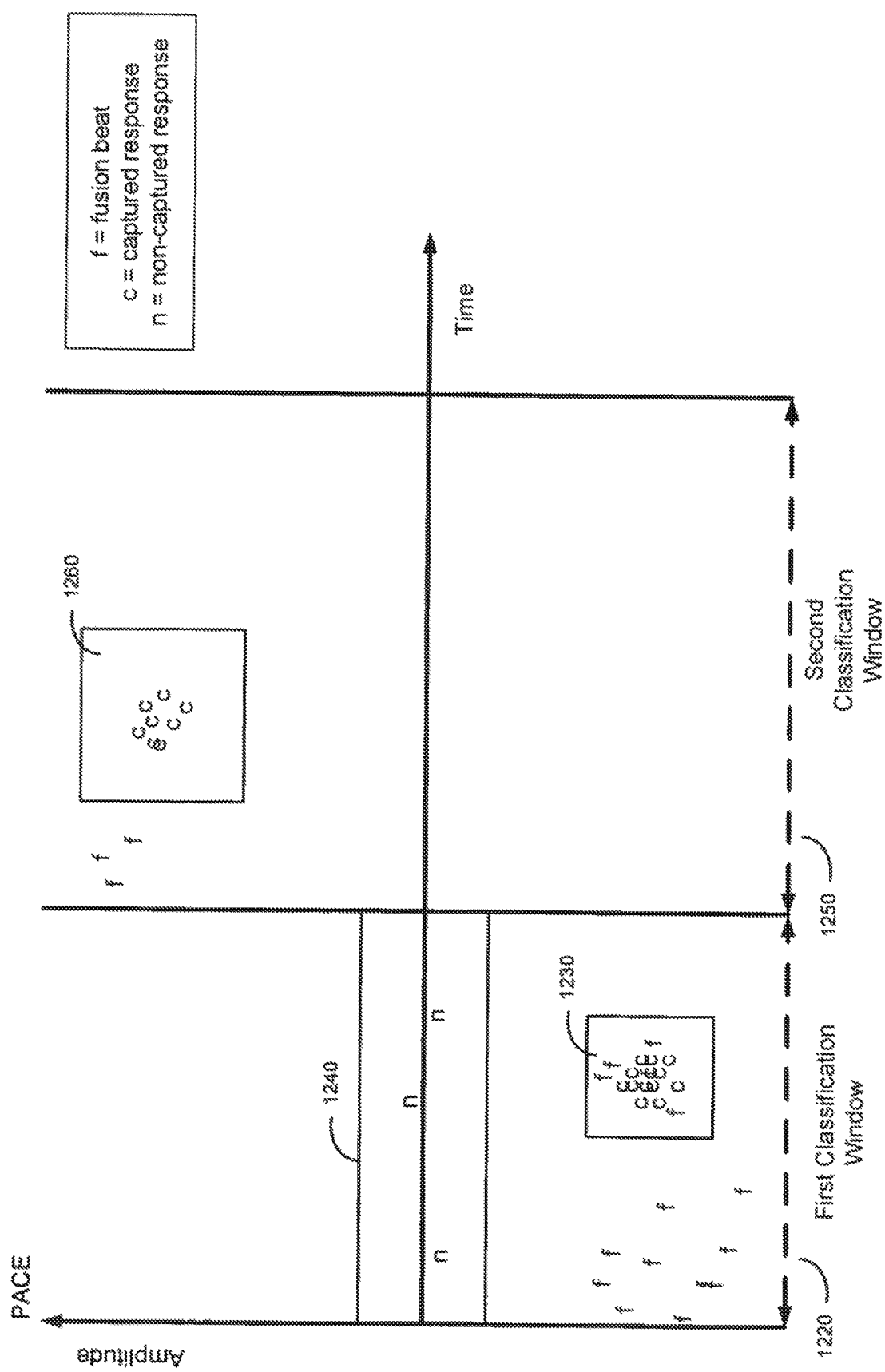
FIG. 12 is a diagram illustrating positions of cardiac signal peaks in relation to the first and second capture detection regions for various cardiac responses in accordance with embodiments of the invention.

FIG. 12 is a diagram illustrating the positions of cardiac signal peaks detected in the first and the second classification windows 1220, 1250 for various cardiac responses in relation to the first and second capture detection regions 1230, 1260. Cardiac responses associated with signal peaks less than or equal to a non-capture threshold 1240 are classified as non-captured responses.

Figure 13A:
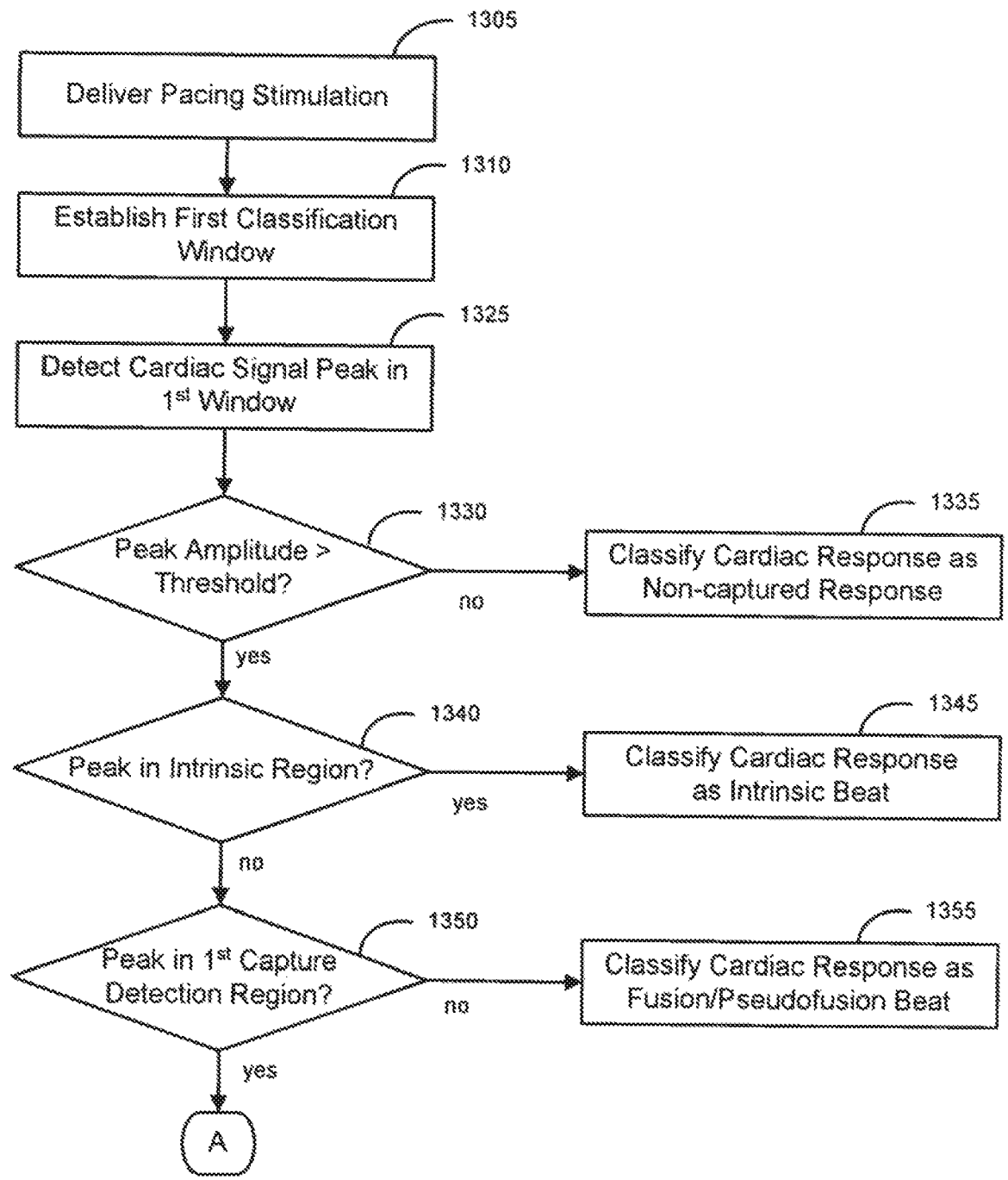
FIGS. 13A and 13B illustrate a flowchart of a method of cardiac response classification including intrinsic response classification in accordance with embodiments of the invention.
Figure 13B:
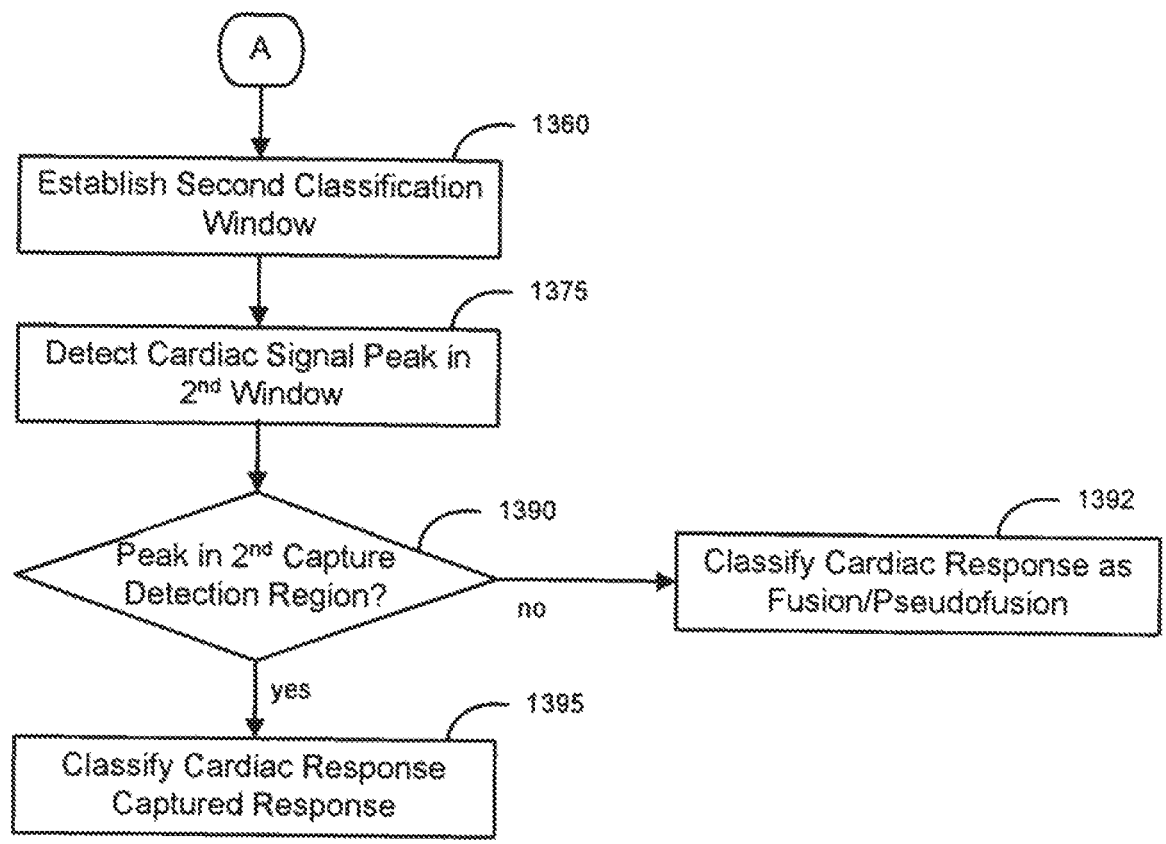

FIGS. 13A and 13B illustrate a flowchart of a method of cardiac response classification including intrinsic response classification in accordance with embodiments of the invention. A pacing stimulation is delivered to the heart 1305. A first classification window is established 1310 subsequent to the pacing stimulation. A cardiac signal peak is detected in the first classification window. If the magnitude of the cardiac signal peak amplitude is less than or equal to 1330 a threshold value, then the cardiac response is classified 1335 as a non-captured response.

If the magnitude of the peak amplitude is greater than 1330 the threshold and the peak is detected 1340 in an intrinsic detection region, then the cardiac response is classified 1345 as a non-captured response combined with an intrinsic beat. If the peak amplitude is greater than 1330 the threshold and the peak is not detected 1350 in a first capture detection region, then the cardiac response is classified as fusion/pseudofusion.

If the peak is detected 1350 in the first capture detection region, then a second cardiac response classification window is established 1360. A peak of the cardiac signal is detected 1375 in the second cardiac response classification window. If the peak of the cardiac signal is not detected 1390 in a second capture detection region, then the cardiac response is classified 1392 as a fusion/pseudofusion. If the peak is detected 1390 in second capture detection region, then the cardiac response is classified as a captured response 1395.

Figure 14:
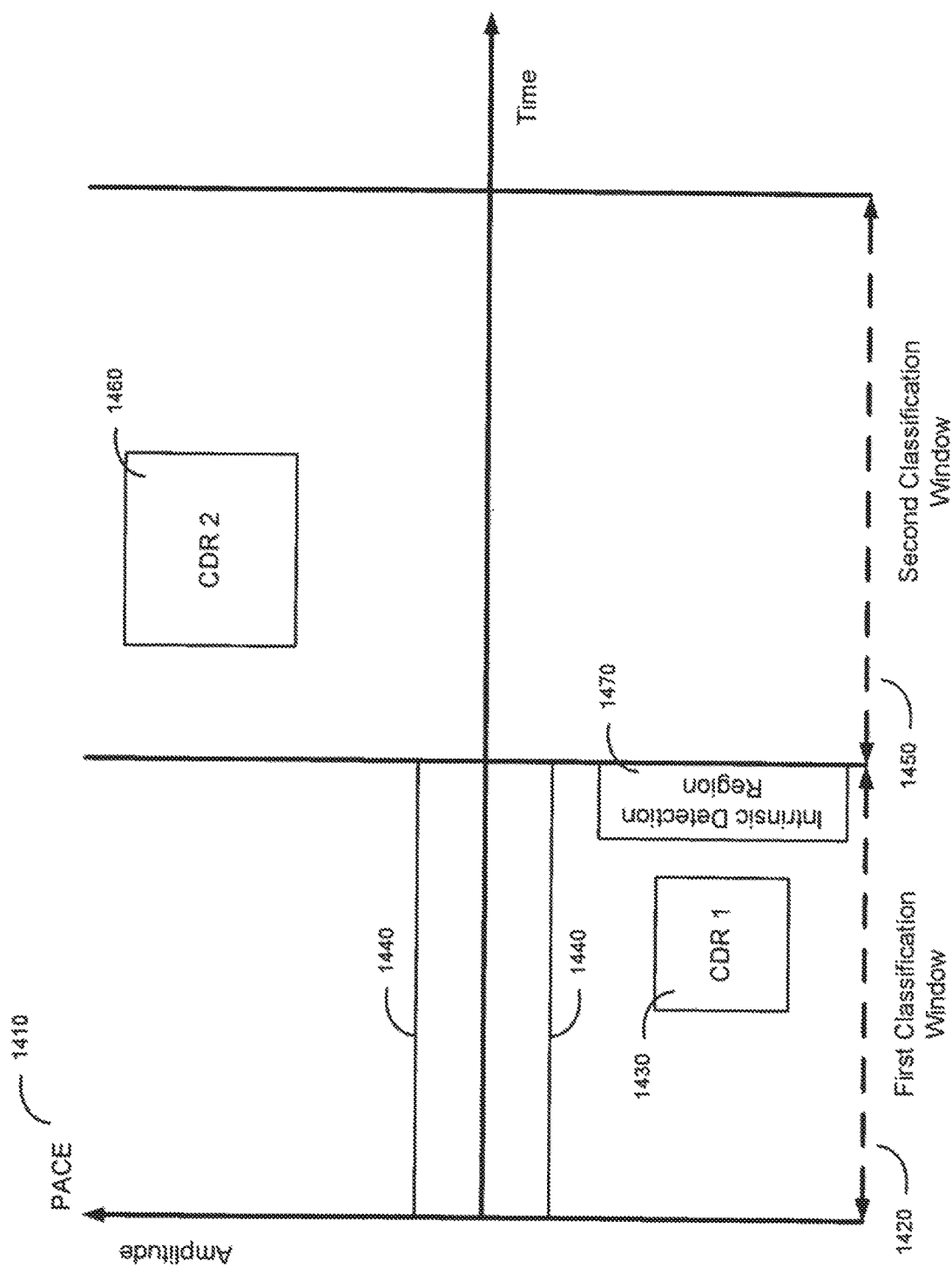
FIG. 14 is a diagram illustrating cardiac response classification windows, capture detection windows, and an intrinsic detection window used to classify a cardiac response to pacing in accordance with embodiments of the invention.

FIG. 14 is a diagram illustrating the cardiac response classification windows, capture detection windows, and the intrinsic detection window described in connection with FIGS. 13A and 13B and used to classify the cardiac response to pacing in accordance with embodiments of the invention. A pacing stimulation 1410 is delivered to the heart and a first cardiac response classification window 1420 is established subsequent to the delivery of the pacing stimulation 1410. A first capture detection region (CDR) 1430 is defined within the first cardiac response classification window. An intrinsic detection region 1470 is defined. The cardiac signal following the pacing stimulation is sensed and the peak amplitude is detected. If the magnitude of the peak is less than or equal to a threshold 1440, then the cardiac response is classified as a non-captured response.

If the peak of the cardiac signal detected in the first cardiac response classification window 1420 is detected in the intrinsic detection region 1470, then the cardiac response is classified as a non-captured response combined with an intrinsic beat.

If the cardiac signal peak falls within the first capture detection region 1430, then a second cardiac response classification window is established 1450. The cardiac signal is sensed in the second cardiac response classification window 1450 and a peak of the cardiac signal is detected. If the peak of the cardiac signal falls within the second capture detection region 1460, then the cardiac response is classified as a captured response.

The cardiac response may be classified as a fusion/pseudofusion beat if the peak of the cardiac signal falls beyond the boundaries of the first capture detection region 1430 and/or beyond the boundaries of the second capture detection region 1460.

Before using the capture detection regions described above, the capture detection regions may be initialized for use. In accordance with various embodiments, an initialization process may involve determining that the morphology of the cardiac signals includes consistent peak information. A number of cardiac signals may be used to determine the boundaries of the capture detection regions.

Figure 15:
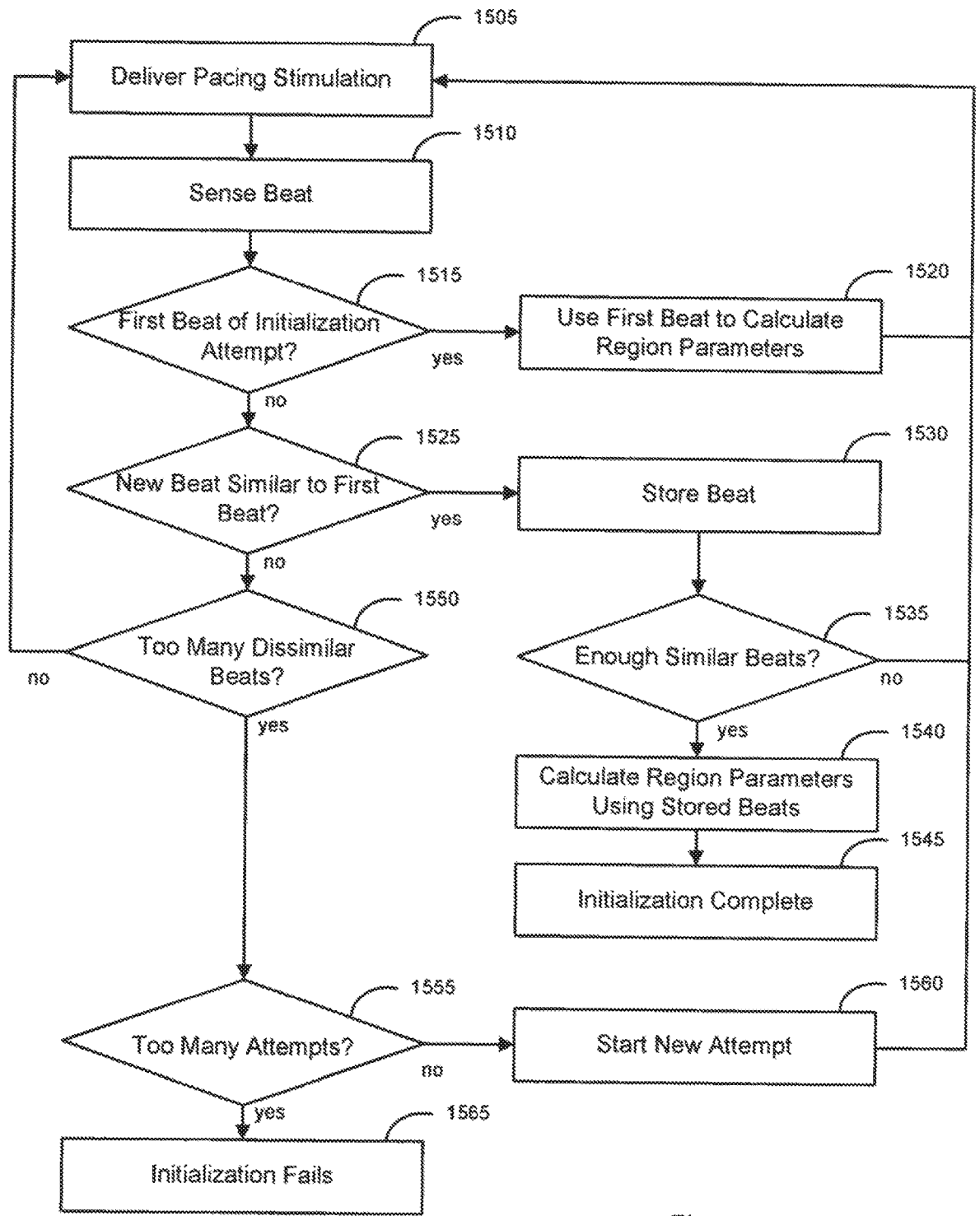
FIG. 15 illustrates a flowchart of a method of initializing detection regions in accordance with embodiments of the invention.

FIG. 15 illustrates a flowchart of a method of initializing detection regions, e.g., capture detection regions and/or intrinsic detection regions, in accordance with embodiments of the invention. The method involves sensing a number of cardiac signals representative of a particular response. If a sufficient number of similar cardiac beats representative of a particular type of pacing response are acquired, then the capture detection region boundaries may be calculated based on the acquired beats.

The detection regions boundaries may be calculated, for example, based on coordinates of characteristic features of the sensed cardiac signals. In one implementation, the average of the characteristic feature coordinates may be defined as a point, such as a center, or other location, within a detection region. In this example, the boundaries of a detection region may be established according to a predetermined shape, for example, a circle, square, rectangle, rhombus, or other quadrilateral. Additionally or alternatively, the detection region may be created to enclose a predetermined area.

After a detection region is initialized, it may be adapted using additional cardiac signal representative of a particular type of cardiac response. Initialization of capture detection regions preferably involves pacing at an energy level sufficient to ensure an adequate number of cardiac signals representative of a captured response. Adaptation of the capture detection regions may involve modification of capture detection region parameters using subsequently acquired cardiac signals representative of a captured response.

Turning now to the initialization process illustrated in FIG. 15, a pacing stimulation is delivered 1505 to the heart and a cardiac beat signal following delivery of the pacing stimulation is sensed 1510. One or more characteristic features of the first beat of the initialization attempt 1515 may be used to calculate 1520 an initial morphology template representative of the type of cardiac response.

If the cardiac beat is not 1515 the first beat in the initialization attempt, then one or more characteristic features of the cardiac beat are compared 1525 to the previously determined template. The comparison may be implemented, for example, by calculating a degree of similarity or correlation between the sensed cardiac beat and the template. If the sensed cardiac beat is similar 1525 to the template, then the sensed cardiac beat is saved 1530.

If enough similar beats are saved 1535, for example, about 7 similar beats out of about 12 beats, then the detection region parameters are calculated 1540 using the stored beats. The initialization attempt is complete 1545.

If the sensed cardiac beat is not similar 1525 to the first beat, and if too many dissimilar beats have been sensed 1550 in the initialization attempt, then another attempt may be initiated 1560. However, if too many previous attempts have been made 1555, then the initialization effort fails 1565.

Figure 16A:
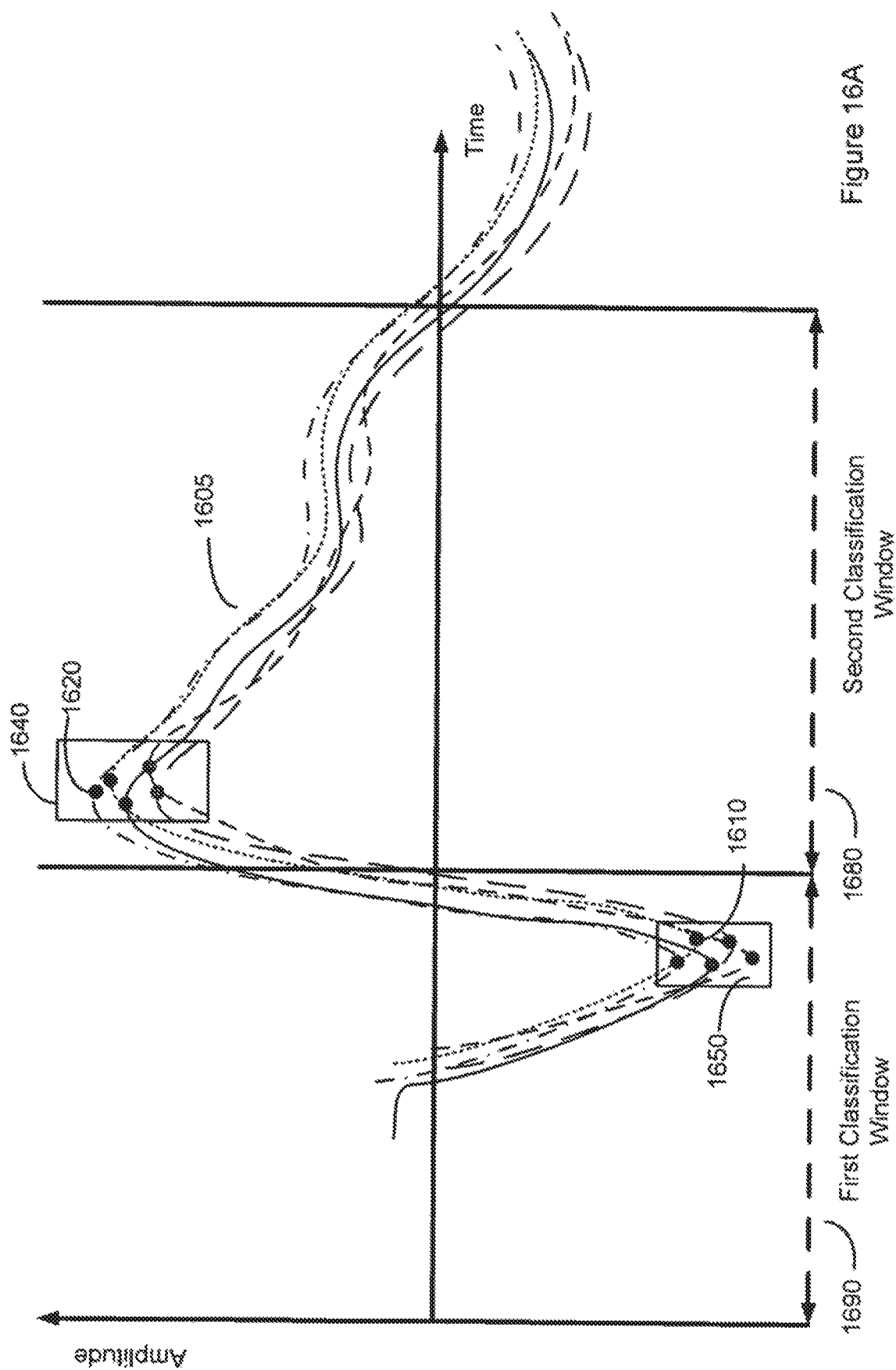
FIG. 16A shows peak locations of five cardiac signal waveforms representing a captured response in accordance with embodiments of the invention.

FIGS. 16A and 16B illustrate a process of initializing the capture detection regions in accordance with an embodiment of the invention. FIG. 16A shows five cardiac signal waveforms 1605 each representing a captured response. Peaks 1610 of the cardiac signal waveforms 1605 are detected in the first cardiac response classification window 1690. The peaks 1610 detected in the first classification window 1690 are used to form the first capture detection region 1650. Peaks 1620 of the cardiac signal waveforms 1605 detected in the second cardiac response classification window 1680 are used to form the second capture detection region 1640.

In accordance with one implementation, the coordinate locations of the peaks detected in a particular classification window may be averaged, and the averaged coordinate location used as a center for the capture detection region. As illustrated in FIG. 16B, the averaged coordinate location 1625 of the coordinate locations of the cardiac signal peaks 1620 detected in the first cardiac response classification window 1690 is used as the center of the first capture detection region 1640. The averaged location 1615 of the coordinate locations of the cardiac signal peaks 1620 detected in the second cardiac response classification window 1680 are used as the center of the second capture detection region 1650.

After initialization of the detection regions, the detection regions may be adapted to accommodate gradual morphological changes in the cardiac signal. A cardiac signal waveform, e.g., a cardiac signal waveform representative of a captured response, may exhibit natural variations in its morphology over time. Unless the detection regions are adjusted, the cardiac waveform morphology may gradually drift away from the originally established detection regions. It may be desirable to adjust the detection regions to track changes in the captured response waveform.

In accordance with embodiments of the invention, one or more of the detection regions may be adapted to changes in cardiac waveform morphology by adjusting the one or more detection regions. A particular detection region may be adjusted according to a relationship, e.g., a spatial relationship, between the particular detection region and its associated waveform feature, for example a peak of the cardiac signal. Adjustment of the detection regions may involve, for example changing the size, shape, or location of the detection region.

A cardiac feature location, such as a peak, may be identified by a timing coordinate (usually represented as an x-axis coordinate) and an amplitude coordinate (y-axis coordinate). A detection region may be adjusted based on a relationship between a detected feature's amplitude coordinate and the associated detection region's amplitude range. A detection region may also be adjusted based on a relationship between an associated detected feature's timing coordinate and the detection region's amplitude range. In other examples, the detection region may be adjusted based on a variability of an associated detected feature's timing and/or amplitude coordinates.

According to embodiments of the invention, the adjustment of a detection region involves modifying the detection region in the direction of an associated cardiac feature location. In various examples, a detected cardiac feature may fall within a particular detection region, but be offset from the center of the detection region. The location, size, and/or shape of the detection region may be modified in the direction of re-centering or otherwise re-orienting the detection region with respect to an associated detected cardiac feature point falling within the detection region. The detection region may be adjusted, for example, using a function-based or rules-based technique.

According to one implementation, adjustment of the detection regions may be accomplished using a function that is based on present and past locations of an associated detected cardiac waveform feature, e.g., a peak. According to one example, the detection region may be adjusted using an exponential average based on the present location of the waveform feature and the previous locations of the detection region. Adjustment of the detection region may be implemented based on Equation 1 below.

$$\text{Adjusted Location} = \forall * \text{Past Location} + (1-\forall) * \text{Current Location} \quad (1)$$

By selecting the values of $\forall$, more emphasis may be placed on the past location of the detection region, corresponding to $\forall > 0.5$, or more emphasis may be placed on the current location, corresponding to $\forall < 0.5$. The value of $\forall$ may vary for different features or characteristics. The location of the detection region may be determined by re-centering or otherwise re-orienting the detection region using the adjusted location.

In other implementations, a detection region may be adjusted using a rules-based technique. For example, the detection region may be adjusted in the direction of a detected associated feature point based on one or more re-centering rules.

A cardiac beat may be required to meet certain qualifications before it is used to adjust the detection regions. A cardiac beat qualified to adjust a detection region may be required to meet certain timing, rate, amplitude, regularity, or other criteria. The cardiac beat may be compared, for example, to a template representing a captured response. If the cardiac beat is consistent with the template, then the cardiac beat may be used to adjust the capture detection regions.

Figure 17B:
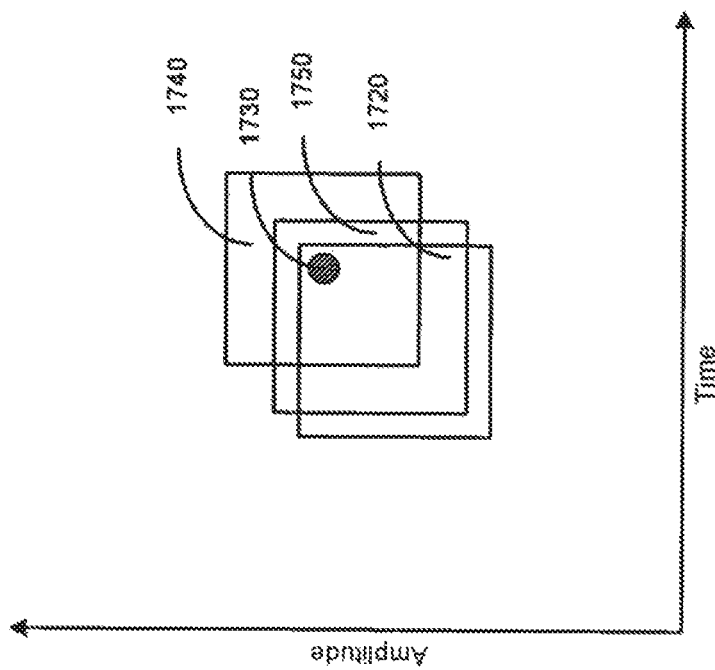
Figure 17A:
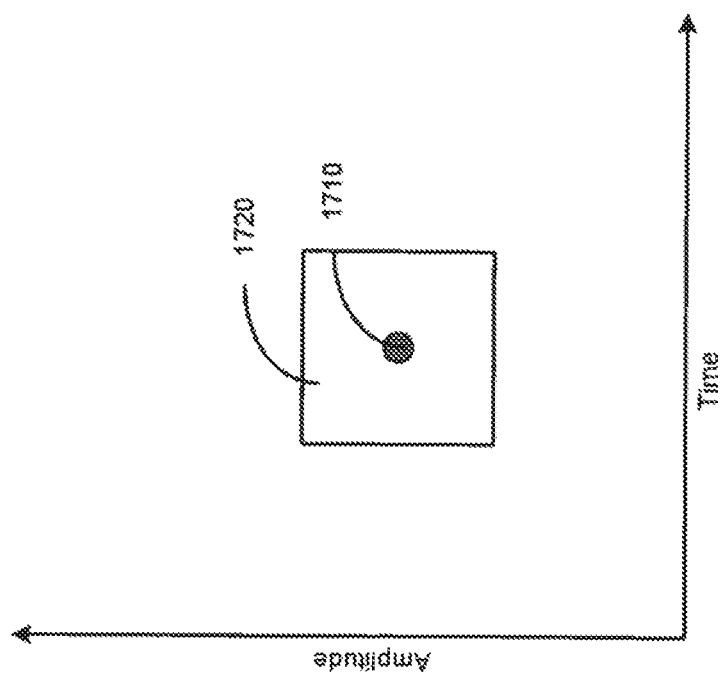

Adjustment of a detection region is illustrated in the diagrams of FIGS. 17A-B. FIG. 17A illustrates a detection region 1720 having a center 1710 based on locations of the previously detected cardiac waveform features associated with the detection region. FIG. 17B illustrates the situation after the next cardiac signal is sensed. The current cardiac waveform feature point 1730 is detected. The location of the current feature point 1730 has drifted above and to the right of the original center 1710 illustrated in FIG. 17A. A current detection region 1740 centered on the new cardiac waveform feature 1730 would represent a significant change from the original detection region 1720. In one example embodiment, adjustment of the detection region is performed so that modifications exhibit a relatively smooth transition. The adjusted detection region 1750 may be determined, for example using Equation 1 or other method, to smoothly accommodate the waveform feature drift based on both the past detection region location 1720 and the current detection region location 1740. The adjustment of the detection region may be limited to predetermined upper and lower boundaries with respect to the amplitude and time coordinates.

Although Equation 1 mathematically describes adjusting the detection region location using an exponential average, other methods of adjusting the detection region locations are also possible. For example, in other embodiments, each of the one or more detection regions may be adjusted according to a moving window average, or another function representing the change in distance between the original detection region and the waveform feature. In a further embodiment, the detection regions may be adjusted according to a rules-based process. A rules-based adjustment process may involve adjusting the detection region location by an amount based on the locations of subsequently detected cardiac waveform features. For example, the detection region location may be moved an incremental amount to the right if a predetermined number, e.g., five, consecutive cardiac signals exhibit cardiac waveform features located within the detection region, but to the right of center of the original detection region. Adjustments in other directions, i.e., left, up, and down, may be made using similar criteria.

Figure 17D:
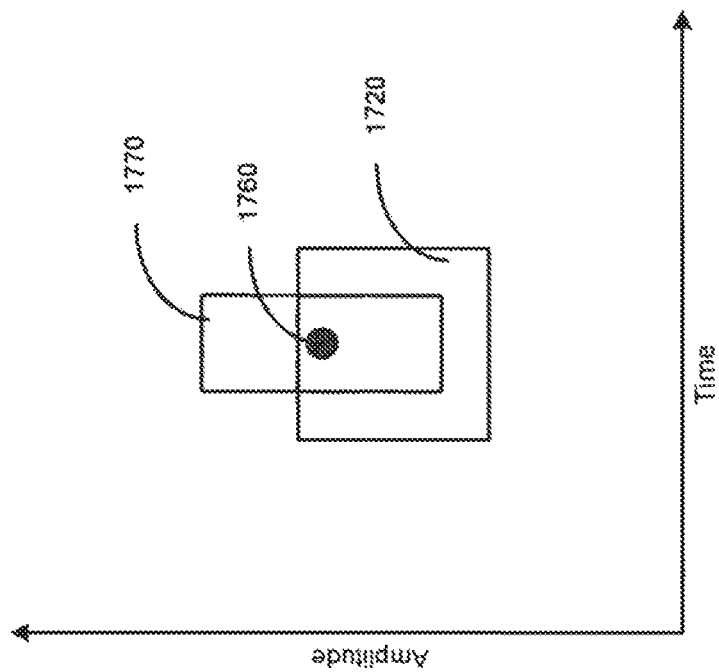
Figure 17C:
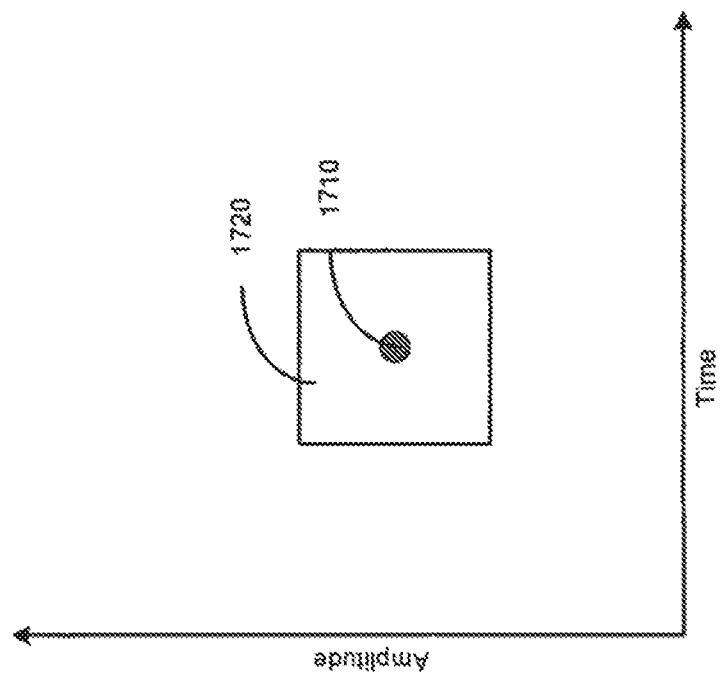

In yet other embodiments, adjustment of a detection region may include adjusting the shape and/or size of the detection region. FIGS. 17C-D are diagrams illustrating adjusting a detection region by modifying the shape of the detection region. FIG. 17C illustrates a detection region 1720 having a center 1710. FIG. 17D illustrates the situation after the next cardiac signal is sensed. The cardiac waveform feature 1760 associated with the detection region 1720 is detected. The location of the current feature point 1760 has drifted above the original center 1710 of the detection region 1720. An adjusted detection region 1770, having a different shape from the original detection region 1720, is defined. The adjustment of the detection region may be limited to a predetermined range with respect to the amplitude and time coordinates.

Embodiments of the invention are directed to methods and systems employing one or more retriggerable cardiac response classification windows. Various embodiments describe discriminating between cardiac response types based on one or more characteristics of the cardiac signal detected the cardiac response classification windows. The use of multiple classification windows for cardiac response classification is described in commonly owned U.S. Patent Application, identified under Attorney Docket Number GUID.045PA, filed Dec. 11, 2003, and incorporated herein by reference in its entirety. Methods and systems for cardiac response classification involving using different pacing and sensing electrode combinations are described in commonly owned U.S. Patent Application, identified under Attorney Docket Number GUID.160PA, filed concurrently with this patent application and incorporated herein by reference in its entirety.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of classifying a cardiac response to a pacing stimulation, comprising:

delivering the pacing stimulation to a first heart chamber;

sensing a cardiac signal of a second heart chamber following delivery of the pacing stimulation;

detecting a first trigger feature of the cardiac signal within a first predetermined capture detection region;

in response to detecting the first trigger feature of the cardiac signal within the first predetermined capture detection region, continuing to evaluate at least a portion of a QRS waveform of the cardiac signal that occurs after the first trigger feature;

classifying the cardiac response as fusion or capture of the second heart chamber based on at least a portion of the QRS waveform of the cardiac signal that occurs after the first trigger feature; and delivering pacing therapy based on the classification of the cardiac response as fusion or capture.

2. The method of claim 1, wherein classifying the cardiac response as fusion or capture comprises:
determining if a second feature of the cardiac signal, which is part of the QRS waveform of the cardiac signal, falls within a second predetermined capture detection region triggered by detection of the first trigger feature within the first predetermined capture region;
classifying the cardiac response as capture if the first trigger feature of the cardiac signal falls within the first capture detection region and the second feature of the cardiac signal falls within the second predetermined capture detection region; and
classifying the cardiac response as fusion if the second feature of the cardiac signal does not fall within the second predetermined capture detection region triggered by detection of the first trigger feature within the first predetermined capture region.

3. The method of claim 1, wherein the first predetermined capture detection region is bounded by upper and lower time boundaries and upper and lower amplitude boundaries.

4. The method of claim 1, wherein:
the first predetermined capture detection region occurs within a first classification window; and
wherein continuing to evaluate the portion of the QRS waveform of the cardiac signal that occurs after the first trigger feature comprises continuing to evaluate the portion of the QRS waveform of the cardiac signal in one or more additional classification windows.

5. The method of claim 1, wherein classifying the cardiac response as fusion or capture comprises discriminating between fusion and capture of the left ventricle.

6. The method of claim 1, wherein classifying the cardiac response as fusion or capture comprises discriminating between fusion and capture of the right ventricle.

7. The method of claim 1, wherein classifying the cardiac response as fusion or capture comprises discriminating between fusion and capture of an atrial chamber.

8. The method of claim 1, further comprising classifying the cardiac response as an intrinsic beat if the first trigger feature of the cardiac signal falls within an intrinsic detection region.

9. The method of claim 8, wherein the intrinsic detection region is bounded by upper and lower time boundaries and upper and lower amplitude boundaries.

10. A cardiac device, comprising:
a pacing pulse generator configured to generate cardiac pacing pulses in a first heart chamber;
a sensing system configured to sense a cardiac pacing response signal of a second heart chamber following delivery of a pacing pulse to the first heart chamber; and
a cardiac response classification system configured to detect a first trigger feature of the cardiac signal within a first classification window, and, in response to detecting the first trigger feature of the cardiac signal, to continue to evaluate at least a portion of a QRS waveform of the cardiac signal that occurs after the first trigger feature, the cardiac response classification system further configured to discriminate between fusion and capture of the second heart chamber based on the portion of the QRS waveform of the cardiac signal that occurs after the first trigger feature.

11. The device of claim 10, further comprising one or more left ventricular electrodes coupled to the sensing system, wherein the second heart chamber is the left ventricle and the cardiac pacing response signal is sensed via the left ventricular electrodes.

12. The device of claim 11, wherein the pacing pulse generator is configured to deliver a back up pace if non capture of the second heart chamber is detected by the cardiac response classification system.

13. The device of claim 10, wherein the pacing pulse is delivered using a first electrode vector and the cardiac pacing response signal is sensed using a second electrode vector.

14. The device of claim 10, wherein the cardiac response classification system is configured to determine if the first trigger feature occurs within a first capture detection region, the first capture detection region bounded by upper and lower time boundaries and upper and lower amplitude boundaries.

15. The device of claim 10, wherein:
the cardiac response classification system is configured to continue to evaluate the cardiac signal in one or more additional classification windows that extend after the first classification window.

16. The device of claim 15, wherein the cardiac response classification system is configured to adapt one or both of an amplitude coordinate and a timing coordinate of the first classification window based on previous captured responses.

17. A system, comprising:
means for delivering pacing stimulation to a first heart chamber;
means for sensing a cardiac signal of a second heart chamber following delivery of the pacing stimulation;
means for detecting a first trigger feature of the cardiac signal within a first predetermined capture detection region;
means for, in response to detecting the first trigger feature of the cardiac signal within the first predetermined capture detection region, continuing to evaluate at least a portion of a QRS waveform of the cardiac signal that occurs after the first trigger feature;
means for classifying the cardiac response as fusion or capture of the second heart chamber based on at least a portion of the QRS waveform of the cardiac signal that occurs after the first trigger feature; and
means for delivering pacing therapy based on the classification of the cardiac response as fusion or capture.

18. The system of claim 17, wherein the means for delivering pacing stimulation to the first heart chamber include a pacing pulse generator configured to generate cardiac pacing pulses in the first heart chamber.

19. The system of claim 17, wherein the means for sensing the cardiac signal of the second heart chamber following delivery of the pacing stimulation include a sensing system configured to sense the cardiac pacing response signal of the second heart chamber following delivery of the pacing pulse to the first heart chamber.

20. The system of claim 17, wherein the means for detecting the first trigger feature of the cardiac signal within the first predetermined capture detection region include a cardiac response classification system configured to detect the first trigger feature of the cardiac signal within the first classification window,
wherein the means for continuing to evaluate at least a portion of a QRS waveform of the cardiac signal that occurs after the first trigger feature include the cardiac response classification system configured to, in response to detecting the first trigger feature of the cardiac signal, continue to evaluate at least a portion of a QRS waveform of the cardiac signal that occurs after the first trigger feature, and wherein the means for classifying the cardiac response as fusion or capture of the second heart chamber based on at least a portion of the QRS waveform of the cardiac signal that occurs after the first trigger feature, include the cardiac response classification system configured to discriminate between fusion and capture of the second heart chamber based on the portion of the QRS waveform of the cardiac signal that occurs after the first trigger feature.

\* \* \* \* \*